United States Patent
Kojima et al.

(10) Patent No.: US 10,959,937 B2
(45) Date of Patent: Mar. 30, 2021

(54) OIL-IN-WATER TYPE ORGANOPOLYSILOXANE EMULSION AND METHOD FOR PRODUCING SAME, COSMETIC RAW MATERIAL, AND COSMETIC PRODUCT

(71) Applicant: Dow Corning Toray Co., Ltd., Tokyo (JP)

(72) Inventors: Kazuhiko Kojima, Chiba (JP); Takatoshi Toyama, Chiba (JP)

(73) Assignee: DOW TORAY CO., LTD., Tokyo (JP)

( * ) Notice: Subject to any disclaimer, the term of this patent is extended or adjusted under 35 U.S.C. 154(b) by 0 days.

(21) Appl. No.: 15/763,255

(22) PCT Filed: Oct. 3, 2016

(86) PCT No.: PCT/JP2016/004450
§ 371 (c)(1),
(2) Date: Mar. 26, 2018

(87) PCT Pub. No.: WO2017/061099
PCT Pub. Date: Apr. 13, 2017

(65) Prior Publication Data
US 2018/0280283 A1  Oct. 4, 2018

(30) Foreign Application Priority Data

Oct. 5, 2015  (JP) .............................. JP2015-197302

(51) Int. Cl.
| | | |
|---|---|---|
| *A61K 8/891* | (2006.01) | |
| *A61K 8/37* | (2006.01) | |
| *A61K 8/39* | (2006.01) | |
| *A61Q 5/02* | (2006.01) | |
| *A61Q 5/12* | (2006.01) | |
| *A61K 8/90* | (2006.01) | |
| *A61K 8/41* | (2006.01) | |
| *A61K 8/49* | (2006.01) | |
| *A61K 8/06* | (2006.01) | |
| *A61K 8/86* | (2006.01) | |

(52) U.S. Cl.
CPC ............... *A61K 8/891* (2013.01); *A61K 8/06* (2013.01); *A61K 8/062* (2013.01); *A61K 8/37* (2013.01); *A61K 8/39* (2013.01); *A61K 8/41* (2013.01); *A61K 8/416* (2013.01); *A61K 8/49* (2013.01); *A61K 8/86* (2013.01); *A61K 8/90* (2013.01); *A61Q 5/02* (2013.01); *A61Q 5/12* (2013.01); *A61K 2800/21* (2013.01); *A61K 2800/596* (2013.01)

(58) Field of Classification Search
CPC combination set(s) only.
See application file for complete search history.

(56) References Cited

U.S. PATENT DOCUMENTS

| | | |
|---|---|---|
| 5,788,884 A | 8/1998 | Kuwata et al. |
| 5,973,066 A | 10/1999 | Sakuta et al. |
| 6,316,541 B1 | 11/2001 | Gee |
| 6,316,545 B1 | 11/2001 | Sakuta |
| 2001/0036450 A1 | 11/2001 | Verite et al. |

FOREIGN PATENT DOCUMENTS

| | | |
|---|---|---|
| EP | 0705864 A1 | 4/1996 |
| JP | H04227932 A | 8/1992 |
| JP | H05132566 A | 5/1993 |
| JP | H09278626 A | 10/1997 |
| JP | H09316331 A | 12/1997 |
| JP | H10306013 A | 11/1998 |
| JP | H11148010 A | 6/1999 |
| JP | H11148011 A | 6/1999 |
| JP | 2000234058 A | 8/2000 |
| JP | 2001261526 A | 9/2001 |
| JP | 2008093581 A | 4/2008 |
| JP | 2009126806 A | 6/2009 |
| WO | 2004069899 A1 | 8/2004 |
| WO | 2013082096 A1 | 6/2013 |

OTHER PUBLICATIONS

PCT/JP2016/004450 International Search Report dated Nov. 15, 2016, 2 pages.
English language abstract and machine translation for JPH05132566(A) extracted from http://worldwide.espacenet.com database on Apr. 25, 2018, 13 pages.
English language abstract and machine translation for JPH09278626(A) extracted from http://worldwide.espacenet.com database on Apr. 25, 2018, 51 pages.
English language abstract and machine translation for JPH10306013(A) extracted from http://worldwide.espacenet.com database on Apr. 25, 2018, 17 pages.
English language abstract and machine translation for JP2008093581(A) extracted from http://worldwide.espacenet.com database on Apr. 25, 2018, 25 pages.

(Continued)

*Primary Examiner* — Hasan S Ahmed
(74) *Attorney, Agent, or Firm* — Warner Norcross + Judd LLP

(57) ABSTRACT

Disclosed is an oil-in-water type organopolysiloxane emulsion that is stable and has smaller particle diameters for a long period of time even in cases where a low-polarity organopolysiloxane and a cationic surfactant are used. The emulsion comprises: (A) 100 parts by weight of a diorganopolysiloxane having a viscosity of 2 to 100,000 mPa·s at 25° C., (B) 0.5 to 30 parts by weight of a cationic surfactant, (C) 0.1 to 10 parts by weight of a nonionic surfactant, and (D) 11 to 550 parts by weight of water, wherein a content of component (C) is equal to or less than a content of component (B), and wherein an average particle diameter of component (A) in the emulsion is 600 nm or less. Related methods and cosmetics are also disclosed.

16 Claims, No Drawings

(56) References Cited

OTHER PUBLICATIONS

English language abstract and machine translation for JP2009126806(A) extracted from http://worldwide.espacenet.com database on Apr. 25, 2018, 28 pages.

Unknown, "Dow Corning AP-8087 Fluid Product Information", Nov. 21, 2013, 4 pages.

Brook, M.A., "Silicon in Organic, Organometallic, and Polymer Chemistry", Wiley: 2000, p. 260-263.

Clarson, S.J. et al., "Siloxane Polymers", PTR Prentice Hall: 1993, p. 22-23.

OIL-IN-WATER TYPE ORGANOPOLYSILOXANE EMULSION AND METHOD FOR PRODUCING SAME, COSMETIC RAW MATERIAL, AND COSMETIC PRODUCT

CROSS-REFERENCE TO RELATED APPLICATIONS

This application is the National Stage of International Application No. PCT/JP2016/004450 filed on 3 Oct. 2016, which claims priority to and all advantages of Japanese Patent Application No. 2015-197302 filed on 5 Oct. 2015, the contents of which are hereby incorporated by reference.

TECHNICAL FIELD

The present invention relates to an oil-in-water type organopolysiloxane emulsion and a method for producing the same. In addition, the present invention relates to a cosmetic raw material composed of the oil-in-water type organopolysiloxane emulsion, and a cosmetic product including the cosmetic raw material.

BACKGROUND ART

Oil-in-water type organopolysiloxane emulsions are used in a wide variety of fields as raw materials for cosmetics, polishes, release agents, fiber treatment agents, and others. Applications especially for cosmetic products make use of oil-in-water type organosiloxane emulsions in which an organopolysiloxane is emulsified with a cationic surfactant, because they are expected to provide a high conditioning effect when formulated into cosmetic products for hair such as shampoos and rinses.

For example, Patent Document 1 discloses an emulsion with an average particle diameter of 1 to 20 microns comprising an organosiloxane, a cationic surfactant, and water. However, such an emulsion was found to be insufficient in terms of storage stability, dilution stability, and formulation stability in preparations, due to its larger average particle diameter.

To address the problem that the diameters of emulsion particles are increased, Patent Documents 2 and 3 employ polyoxyalkylene-modified silicones. However, these silicones still resulted in the generation of emulsions with an average particle diameter ranging from 1 to 20 microns, and particles having particle diameters out of this range were removed from the viewpoints of the stability as emulsions and the adhesion onto hair when they were formulated into cosmetic articles.

In addition, Patent Document 4 discloses that an emulsion having an average particle diameter of 300 nm or less can be prepared by emulsifying a polyether-modified silicone that undergoes gelation and a cationic surfactant using a liquid crystal emulsification method. However, the preparation process disclosed therein gives rise to a problem that an emulsion having a smaller average particle diameter cannot be prepared when a low-polarity diorganopolysiloxane such as dimethylpolysiloxane is used instead of the polyether-modified silicone.

CITATIONS LIST

Patent Literature

Patent Literature 1: JP H09-316331 A
Patent Literature 2: JP H11-148010 A
Patent Literature 3: JP H11-148011 A
Patent Literature 4: JP 2008-093581 A

SUMMARY OF INVENTION

Technical Problems

An object of the present invention is to provide a low-polarity organopolysiloxane emulsion that has smaller particle diameters and is stable for a long period of time even in cases where a cationic surfactant is used.

Solutions to Problems

According to an aspect, an oil-in-water type organopolysiloxane emulsion of the present invention comprises the following components:
(A) 100 parts by weight of a diorganopolysiloxane having a viscosity of 2 to 100,000 mPa·s at 25° C., (B) 0.5 to 30 parts by weight of a cationic surfactant, (C) 0.1 to 10 parts by weight of a nonionic surfactant, and (D) 11 to 550 parts by weight of water, wherein a content of the component (C) is equal to or less than a content of the component (B), and an average particle diameter of the component (A) in the emulsion is 600 nm or less.

The component (B) preferably is at least one quaternary ammonium salt selected from the group consisting of stearyltrimethylammonium chloride, distearyldimethylammonium chloride, stearyldimethylbenzylammonium chloride, dioleyldimethylammonium chloride, behenyltrimethylammonium chloride, dibehenyldimethylammonium chloride, and behenyldimethylbenzylammonium chloride.

The component (C) preferably is at least one nonionic surfactant selected from the group consisting of a sorbitan fatty acid ester, a polyoxyethylene sorbitan fatty acid ester, a polyoxyethylene sorbitol fatty acid ester, a glycerin fatty acid ester, a polyoxyethylene hydrogenated castor oil, a polyglycerin fatty acid ester, and a polyoxyethylene-polyoxypropylene block copolymer.

The oil-in-water type organopolysiloxane emulsion of the present invention preferably further includes (E) 0.1 to 20 parts by weight of an alcohol, relative to 100 parts by weight of the component (A).

The oil-in-water type organopolysiloxane emulsion as defined above preferably has octamethylcyclotetrasiloxane and decamethylcyclopentasiloxane of which the respective contents are 0.5% or less by weight.

According to another aspect, a method for producing an oil-in-water type organopolysiloxane emulsion of the present invention is characterized in that the method includes emulsifying under shear force the following components:
(A) 100 parts by weight of a diorganopolysiloxane having a viscosity of 2 to 100,000 mPa·s at 25° C., (B) 0.5 to 30 parts by weight of a cationic surfactant,
(C) 0.1 to 10 parts by weight of a nonionic surfactant, and (D) 1 to 50 parts by weight of water, wherein an amount of the component (C) is equal to or less than an amount of the component (B), and an amount of the component (D) is 3 times or less than a combined amount of the components (B) and (C), thereby to prepare an oil-in-water type organopolysiloxane emulsion, and then adding, to the resulting emulsion, 10 to 500 parts by weight of water, followed by subjecting a mixture to phase inversion emulsification.

According to another aspect, a cosmetic raw material of the present invention is composed of an above-described oil-in-water type organopolysiloxane emulsion, and preferably is a raw material for a hair cosmetic product.

According to another aspect, a cosmetic product of the present invention is characterized by including an above-described cosmetic raw material.

Advantageous Effects of Invention

According to the present invention, it is possible to provide an organopolysiloxane emulsion that is stable and has smaller particle diameters for a long period of time, even in cases where a cationic surfactant is used. According to the present invention, it is also possible to provide an organopolysiloxane emulsion with particle diameters of 600 nm or less that has a lower degree of irritation, includes a smaller content of octamethylcyclotetrasiloxane or decamethylcyclopentasiloxane, and exhibits good stability.

DESCRIPTION OF EMBODIMENTS

First, the oil-in-water type organopolysiloxane emulsion of the present invention will be described in detail.

Component (A) is a main component of the emulsion of the present invention and is diorganopolysiloxane having a viscosity at 25° C. of 2 to 100,000 mPa·s, preferably 5 to 70,000 mPa·s, or 10 to 50,000 mPa·s. This is because when the viscosity at 25° C. is at least the lower limit of the above range, adhesion to the substrate such as hair and fiber is good in using the emulsion as a hair cosmetic product or a fiber treating agent, while when the viscosity at 25° C. is less than or equal to the upper limit of the above range, the average particle diameter of the diorganopolysiloxane in the emulsion can be made smaller, so that the stability of the emulsion can be improved. The viscosity of the component (A) at 25° C. can be measured by a rotational viscometer according to JIS K7117-1.

In the diorganopolysiloxane of the component (A), examples of the group bonded to the silicon atom include an alkyl group having 1 to 20 carbon atoms, such as a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, and a nonadecyl group; a cycloalkyl group having 5 to 20 carbon atoms, such as a cyclopentyl group and a cyclohexyl group; an alkenyl group having 2 to 20 carbon atoms, such as a vinyl group, a propenyl group, and a hexenyl group; an aryl group having 6 to 20 carbon atoms, such as a phenyl group, a tolyl group, and a naphthyl group; an aralkyl groups having 7 to 20 carbon atoms, such as a benzyl group and a phenethyl group; a group in which some or all of the hydrogen atoms in these hydrocarbon groups have been substituted with a halogen atom such as fluorine; a small amount of hydroxyl groups; and further an alkoxy group having 1 to 5 carbon atoms, such as a methoxy group, an ethoxy group, and a propoxy group. It is preferred that at least 70 mol %, in particular at least 90 mol %, of the groups bonded to silicon atoms in the component (A) is methyl groups.

The molecular structure of the component (A) is linear, and a part thereof may have a branch. Examples of such component (A) include dimethylpolysiloxane having molecular chain both ends blocked with hydroxy groups; a dimethylsiloxane-methylvinylsiloxane copolymer having molecular chain both ends blocked with hydroxy groups; a methylphenylpolysiloxane having molecular chain both ends blocked with hydroxy groups; a dimethylsiloxane-methylphenylsiloxane copolymer having molecular chain both ends blocked with hydroxy groups; a dimethylpolysiloxane having molecular chain both ends blocked with trimethylsiloxy groups; a dimethylsiloxane-methylvinylsiloxane copolymer having molecular chain both ends blocked with trimethylsiloxy groups; a methylphenylpolysiloxane having molecular chain both ends blocked with trimethylsiloxy groups; a dimethylsiloxane-methylphenylsiloxane copolymer having molecular chain both ends blocked with trimethylsiloxy groups; a dimethylpolysiloxane having molecular chain both ends blocked with trimethylsiloxy groups; a dimethylsiloxane-methylvinylsiloxane copolymer having molecular chain both ends blocked with dimethylvinylsiloxy groups; a methylphenylpolysiloxane having molecular chain both ends blocked with dimethylvinylsiloxy groups; a dimethylsiloxane-methylphenylsiloxane copolymer having molecular chain both ends blocked with dimethylvinylsiloxy groups; and mixtures of at least two of these, or mixtures of diorganopolysiloxanes having different viscosities at 25° C. In the emulsifier of the present invention, when at least two kinds of the diorganopolysiloxanes having different viscosities at 2° C. are mixed as the component (A), as a result, it is preferred that the viscosity of the mixture at 25° C. falls within the above range.

The polymerization degree of the siloxane of component (A) is preferably low polymerization, and specifically, the average polymerization number of the siloxane unit is preferably 5 to 1,000, more preferably 10 to 850.

Component (B) is a cationic surfactant for emulsifying the component (A), and specific examples thereof include alkyl quaternary ammonium salts, such as lauryl trimethyl ammonium chloride, myristyl trimethyl ammonium chloride, palmityl trimethyl ammonium chloride, stearyl trimethyl ammonium chloride, distearyl dimethyl ammonium chloride, stearyl dimethylbenzyl ammonium chloride, dioleyl dimethyl ammonium chloride, oleyl trimethyl ammonium chloride, cetyl trimethyl ammonium chloride, behenyl trimethyl ammonium chloride, dibehenyl dimethyl ammonium chloride, behenyl dimethylbenzyl ammonium chloride, coconut oil alkyl trimethyl ammonium chloride, tallow alkyl methyl ammonium chloride, stearyl trimethyl ammonium bromide, coconut alkyl trimethyl ammonium bromide, cetyl trimethyl ammonium methosulfate, oleyl dimethylethyl ammonium ethosulfate, dioctyl dimethyl ammonium chloride, dilauryl dimethyl ammonium chloride, distearyl dimethyl ammonium chloride, and octadecyl diethylmethyl ammonium sulfate; (polyoxyalkylene)alkylamino ether salts, such as (polyoxyethylene)lauryl amino ether lactate, stearyl amino ether lactate, di(polyoxyethylene) lauryl methylamino ether dimethyl phosphate, di(polyoxyethylene) lauryl ethyl ammonium ethosulfate, di(polyoxyethylene) hardened beef tallow alkyl ethylamine ethosulfate, di(polyoxyethylene) lauryl methyl ammonium dimethyl phosphate, and di(polyoxyethylene) stearylamine lactate; acylamidoalkyl quaternary ammonium salts, such as N-(2-hydroxyethyl)-N,N-dimethyl-N-stearoylamidopropyl ammonium nitrate, lanolin fatty acid amido propylethyldimethyl ammonium ethosulfate, and lauroylamidoethylmethyldiethyl ammonium methosulfate; alkyl ethenoxy quaternary ammonium salts, such as dipalmityl polyethenoxyethyl ammonium chloride and distearyl polyethenoxymethyl ammonium chloride; benzalkonium salts, such as lauryl dimethylbenzyl ammonium chloride and stearyl dimethylbenzyl ammonium chloride; benzethonium salts, such as benzyldimethyl {2-[2-(p-1,1,3,3-tetramethylbutylphenoxy) ethoxhyl} ammonium chloride; pyridinium salts such as cetylpyridinium chloride; imidazolinium salts, such as oleyl hydroxyethyl imidazolinium ethosulfate and lauryl hydroxyethyl imidazolinium ethosulfate; acylated basic amino acid alkyl ester salts, such as N-cocoyl-arginine ethyl ester pyrrolidone carboxylate, N-lauroyl-lysine ethyl ethyl ester chloride; primary amine salts such as laurylamine chloride, stearylamine bromide, hardened beef tallow alkylamine chloride, and rosin amine acetate; secondary amine salts such as cetylmethylamine sulfate, laurylmethylamine chloride, dilaurylamine acetate, stearylethylamine bromide, laurylpropylamine acetate, dioctylamine chloride, and octadecylethylamine hydroxide; tertiary amine salts such as dilaurylmethylamine sulfate, lauryldiethylamine chloride, laurylethylmethylamine bromide, diethanol stearylamidoethylamine trihydroxyethyl phosphate, and stearylamidoethylethanolamine urea polycondensate acetic acid salt; laurylmethylamine chloride, dilaurylamine acetate; fatty acid amide guanidinium salts; alkyltrialkylene glycol ammonium salts such as lauryl triethylene glycol ammonium hydroxide, and mixtures of at least two of these.

In particular, from the viewpoints of safety such as skin irritation, emulsifying power and suppliability, the component (B) is preferably at least one quaternary ammonium salt selected from the group consisting of stearyl trimethyl ammonium chloride, distearyl dimethyl ammonium chloride, stearyl dimethylbenzyl ammonium chloride, behenyl trimethyl ammonium chloride, dibehenyl dimethyl ammonium chloride, and behenyl dimethylbenzyl ammonium chloride, and in particular, stearyl trimethyl ammonium chloride and behenyl trimethyl ammonium chloride are preferable.

Such a component (B) can be added as a water-containing substance or an organic solvent-containing substance such as an alcohol, and it is particularly preferable to add it as an alcohol-containing substance. Examples of the alcohol include monovalent lower alcohols such as ethanol, n-propanol, isopropanol, and n-butanol; dihydric alcohols such as 1,3-butylene glycol, ethylene glycol, and propylene glycol; polyalkylene glycols such as polyethylene glycol, dipropylene glycol, and polypropylene glycol; polyhydric alcohols such as glycerin, diglycerin, trimethylolpropane, pentaerythritol, and sorbitol. Most preferably, ethanol and isopropanol are exemplified. The content of alcohol in the component (B) is such that the weight ratio of cationic surfactant:alcohol is 100:5 to 100:200, 100:10 to 100:150, or 100:15 to 100:100.

The content of the component (B) is 0.5 to 30 parts by weight, preferably 1 to 25 parts by weight, or 2 to 20 parts by weight, with respect to 100 parts by weight of the component (A). This is because when the content of the component (B) is at least the lower limit of the above range, it is possible to obtain an emulsified product having an intended average particle diameter, thereby improving the stability of the emulsion, while when the content of the component (B) is less than or equal to the upper limit of the above range, stickiness of hair and fiber to the base material is hard to occur and the feel is good in using the obtained emulsion as a hair cosmetic product or a fiber treating agent or the like.

Component (C) is a nonionic surfactant for emulsifying the component (A) together with the component (B), and specific examples thereof include polyoxyalkylene linear alkyl ethers such as polyoxyethylene hexyl ether, polyoxyethylene octyl ether, polyoxyethylene decyl ether, polyoxyethylene lauryl ether, and polyoxyethylene cetyl ether; polyoxyalkylene branched primary alkyl ethers such as polyoxyethylene 2-ethylhexyl ether, polyoxyethylene isocetyl ether, and polyoxyethylene isostearyl ether; polyoxyalkylene branched secondary alkyl ethers such as polyoxyethylene 1-hexyl hexyl ether, polyoxyethylene 1-octyl hexyl ether, polyoxyethylene 1-hexyl octyl ether, polyoxyethylene 1-pentyl heptyl ether and polyoxyethylene 1-heptyl pentyl ether; polyoxyalkylene alkenyl ethers such as polyoxyethylene oleyl ether; polyoxyalkylene alkylphenyl ethers such as polyoxyethylene octyl phenyl ether, polyoxyethylene nonyl phenyl ether, and polyoxyethylene dodecyl phenyl ether; polyoxyalkylene alkylaryl phenyl ethers such as polyoxyethylene tristyryl phenyl ether, polyoxyethylene distyryl phenyl ether, polyoxyethylene styryl phenyl ether, polyoxyethylene tribenzyl phenyl ether, polyoxyethylene dibenzyl phenyl ether, and polyoxyethylene benzyl phenyl ether; polyoxyalkylene fatty acid esters such as polyoxyethylene monolaurate, polyoxyethylene monooleate, polyoxyethylene monostearate, polyoxyethylene monomyristylate, polyoxyethylene dilaurate, polyoxyethylene dioleate, polyoxyethylene dimyristylate, and polyoxyethylene distearate; sorbitan esters such as sorbitan monopalmitate and sorbitan monooleate; polyoxyalkylene sorbitan fatty acid esters such as polyoxyethylene sorbitan monostearate and polyoxyethylene sorbitan monooleate; glycerine fatty acid esters such as glycerin monostearate, glycerin monolaurate, and glycerin monopalmitate; polyglycerin fatty acid esters such as polyglyceryl monolaurate, polyglyceryl monostearate, and polyglyceryl monooleate; polyoxyalkylene sorbitol fatty acid esters; sucrose fatty acid esters; polyoxyalkylene castor oil ethers such as polyoxyethylene castor oil ether; polyoxyalkylene hardened castor oil ethers such as polyoxyethylene hardened castor oil ether; polyoxyalkylene alkylamino ethers such as polyoxyethylene lauryl amino ether and polyoxyethylene stearyl amino ether; oxyethylene-oxypropylene block or random copolymer; terminal alkyl ethers of oxyethylene-oxypropylene block or random copolymers; terminal sucrose ethers of oxyethylene-oxypropylene block or random copolymers; and mixtures of at least two of them. In particular, sorbitan fatty acid esters, polyoxyethylene sorbitan fatty acid esters, polyoxyethylene sorbitol fatty acid esters, glycerin fatty acid ester, polyoxyethylene hardened castor oil, polyglycerin fatty acid esters, and polyoxyethylene-polyoxypropylene block copolymer are preferable, and polyoxyethylene sorbitan fatty acid esters, polyoxyethylene sorbitol fatty acid esters, polyoxyethylene hardened castor oil, polyglycerin fatty acid esters, and polyoxyethylene-polyoxypropylene block copolymers are also preferable.

From the viewpoints of storage stability, dilution stability, and formulation stability when formulated into a preparation, the component (C) has an HLB value of 6 to 19, more preferably 9 to 18.5. Here, HLB (hydrophilic-lipophilic balance) is the Griffin's HLB determined by the following formula:

HLB=(Molecular weight of hydrophilic group/Total molecular weight)×(100/5)={Hydrophilic substrate amount/(Hydrophobic substrate amount+ Hydrophilic substrate amount)}×(100/5)

The content of the component (C) is from 0.1 to 10 parts by weight, preferably from 0.2 to 8 parts by weight, or from 0.25 to 6 parts by weight, with respect to 100 parts by weight of the component (A). This range of such a content is set from the fact that when the content of the component (C) is at least the lower limit of the above range, it is possible to obtain an emulsified product having an intended average particle diameter, thereby improving the stability of the emulsion, while when the content of the component (C) is less than or equal to the upper limit of the above range and the obtained emulsion is used as a hair cosmetic product or a fiber treating agent or the like, stickiness of hair and fiber to the base material is hard to occur, resulting in good feeling.

From the viewpoint of formulation stability in the preparation, the amount of the component (C) used is equal to or less than the amount of the component (B) used, preferably one third or less of the amount of the component (B) used, or one fifth or less of the amount of the component (B) used.

The component (D) is water for dispersing the component (A), and such water is not limited as long as it does not contain a component that inhibits the storage stability of the emulsification and the emulsion. Specific examples thereof include ion exchanged water, distilled water, well water, and tap water. In order to obtain a desired particle diameter, the component (D) is blended in an amount of 1 to 50 parts by weight, preferably 1 to 30 parts by weight, based on 100 parts by weight of the component (A) before the phase inversion emulsification. A part or the whole amount of the component (D) can also be used for dissolving or dispersing the component (B) or the component (C), and when the component (B) or the component (C) is a commercially available product containing water, it contains a part or the whole of the component (D).

In order to obtain a desired particle size, the component (D) is preferably 3 times or less, more preferably 2 times or less, of the total amount of the component (B) and the component (C). The emulsified product of the present invention can be diluted with a discretionary amount of water depending on workability, application, etc., and specifically water in an amount of 10 to 500 parts by weight based on 100 parts by weight of the component (A) can be added.

The composition of the present invention may contain an alcohol (E) as an optional component in an amount of 0.1 to 20 parts by weight based on 100 parts by weight of the component (A). Examples of the alcohol include monovalent lower alcohols such as ethanol, n-propanol, isopropanol, and n-butanol; dihydric alcohols such as 1,3-butylene glycol, ethylene glycol, and propylene glycol; polyalkylene glycols such as polyethylene glycol, dipropylene glycol, and polypropylene glycol; polyhydric alcohols such as glycerin, diglycerin, trimethylolpropane, pentaerythritol, and sorbitol; and mixtures of at least two of them. Most preferred as the component (E) are ethanol and isopropanol.

These alcohols can also be used when adding the cationic surfactant of the component (B) described above.

In the emulsion of the present invention, the average particle diameter (so-called volume average particle diameter) of the component (A) as measured by a dynamic light scattering method is 600 nm or less, preferably 500 nm or less, or 450 nm or less, from the viewpoints of storage stability, formulation stability in a preparation, and dilution stability.

Further, the emulsion of the present invention is preferably such that each content of octamethylcyclotetrasiloxane and decamethylcyclopentasiloxane is preferably 0.5% by weight or less, 0.25% by weight or less, or 0.1% by weight or less. This content can be measured by gas chromatography.

The pH of the emulsion of the present invention is not limited, but is preferably 4.5 to 8, 5 to 7.5, or 5.5 to 7. This is because when the pH of the emulsion is at least the lower limit of the above range, the stability when blended in the preparation is good, whereas if the pH is below the upper limit of the above range, each content of the octamethylcyclotetrasiloxane and decamethylcyclopentasiloxane is reduced with time.

In the emulsion of the present invention, if necessary, other components, such as a thickener, an antifoaming agent, a penetrant, an antistatic agent, an inorganic powder, an antiseptic, antirust agent, a pH adjuster, a buffer, an ultraviolet absorber, a water-soluble resin, an organic resin emulsion, a pigment, a dye, an antibacterial agent, a deodorant, a humectant, an antioxidant, a chelating agent, etc., may be added within the range not to impair the object of the present invention. It is also possible to dilute the emulsion of the present invention with a discretionary amount of water depending on the purpose of use.

The emulsion of the present invention can be prepared by emulsifying the above-mentioned components (A) to (D) and optionally other additives by mechanical force using an emulsifying machine such as a paddle stirrer, a propeller stirrer, a Henschel type mixer, a planetary mixer, a homomixer, a colloid mill, a combination mixer, an inline type continuous emulsifying machine, a vacuum emulsifying machine, and a continuous mixer.

The production method of the emulsion of the present invention is a production method including the following three steps.

1. A step of preparing a mixture containing:
   (A) 100 parts by weight of an organopolysiloxane,
   (B) 0.5 to 30 parts by weight of a cationic surfactant,
   (C) 0.1 to 10 parts by weight of a nonionic surfactant,
   (D) 1 to 50 parts by weight of water,
   (E) 0 to 20 parts by weight of an alcohol, and an optional component.

At this time, the amount of the component (C) used is preferably equal to or less than the amount of the component (B) used, more preferably one-third or less of the component (B), more preferably one-fifth or less of the amount of the component (B) used.

The component (D) is preferably 3 times or less, more preferably 2 times or less the total amount of the component (B) and the component (C). When the component (D) is three times or more the total amount of the component (B) and the component (C), sufficient shearing force cannot be given during phase inversion emulsification under high shear force in the second step and it becomes impossible to obtain a desired emulsion of 600 nm or less, or 500 nm or less, or 450 nm or less.

In addition, the component (B) can be added by mixing with the component (E) in advance, and a commercially available product obtained by mixing the component (B) and the component (E) can also be used. In particular, in the case of a quaternary ammonium salt containing an alkyl group having 18 or more carbon atoms as the component (B), its dispersibility in water is remarkably deteriorated, so that the amount of the component (D) to be used is increased in order to uniformly disperse the component (B) in the step 1 without using the component (E). Thus, a sufficient shear force cannot be imparted upon the phase inversion emulsification, so that a small particle diameter emulsion cannot be obtained. The component (E) is preferably contained in an amount of 0.1 to 20 parts by weight in order to uniformly disperse the mixture in the step 1.

2. A step of phase inversion emulsification from a water-in-oil type to an oil-in-water type under high shear force.

3. A step of further adding 10 to 500 parts by weight of dilution water to obtain an emulsion having an average particle size of 600 nm or less.

The oil-in-water type organopolysiloxane emulsion of the present invention can be suitably used as a cosmetic raw material. Cosmetic products which can be blended with the oil-in-water type organopolysiloxane emulsion of the present invention are not limited, and examples thereof include skin cosmetic products such as skin cleanser, skin care cosmetic articles, makeup cosmetic articles, antiperspirant, and ultraviolet protective agent; hair cosmetic products such as hair cleanser, hair dressing, hair coloring agent, hair tonic, and hair rinse; bath cosmetic products; others (e.g. perfume and cologne), among which hair cosmetic products are particularly preferred Examples of the hair cosmetic products which can incorporate the oil-in-water type organopolysiloxane emulsion of the present invention include hair cleansing agents such as shampoo and rinse-in sharpener; hair dressings such as hair oils, hair curling retention agents, setting agents, hair creams, hair sprays, hair styling liquids, and hair waxes; hair coloring agents such as hair dyes, hair color sprays, hair color rinses, and hair color sticks; hair growers such as hair tonics, hair treatment agents, and hair packs; hair rinses such as hair conditioners, oil rinses, cream rinses, and treatment rinses.

The blending amount of the cosmetic raw material of the present invention in the cosmetic may be 0.01 to 20 parts by weight, preferably 0.1 to 15 parts by weight, more preferably 0.3 to 12 parts by weight, based on 100 parts by weight of the entire cosmetic product.

The cosmetic raw material of the present invention includes the above-mentioned polyorganosiloxane emulsion, but in order to further improve the blending stability in cosmetic products, it is possible to add other ingredients known as additives for cosmetic raw materials including a silicone emulsion as long as the object of the present invention is not impaired. Examples of such additives include nonionic surfactants other than the component (C), pH adjusters, preservatives, antifungal agents, antirust agents and the like. These components can be used singly or in combination of two or more thereof. The order of blending these components is not particularly limited, but it is preferable to limit the addition amount of the components that delay or interfere with the emulsion polymerization like nonionic surfactants, or it is preferable to blend such nonionic surfactants after emulsion polymerization.

Specific examples of the pH adjuster include hydrochloric acid, sulfuric acid, phosphoric acid, diammonium hydrogenphosphate, disodium hydrogenphosphate, dipotassium hydrogen phosphate, ammonium dihydrogenphosphate, sodium dihydrogenphosphate, potassium dihydrogenphosphate, trisodium phosphate, tripotassium phosphate, acetic acid, ammonium acetate, sodium acetate, potassium acetate, citric acid, sodium citrate, diammonium citrate, sodium carbonate, potassium carbonate, ammonium carbonate, sodium bicarbonate, ammonium bicarbonate, sodium hydroxide, potassium hydroxide, ammonia, and triethanolamine.

Specific examples of the antiseptic, antifungal agent, and antirust agent include benzoic acid, aluminum benzoate, sodium benzoate, isopropylmethylphenol, ethylhexanediol, lysozyme chloride, chlorhexidine hydrochloride, octylphenoxyethanol, orthophenylphenol, sodium perborate, photosensitizer 101, photosensitizer 201, photosensitizer 301, photosensitizer 401, chlorhexidine gluconate solution, cresol, chloramine T, chloroxylenol, chlorocresol, chlorphenesin, chlorhexidine, chlorobutanol, resorcinol acetate, salicylic acid, sodium salicylate, domiphen bromide, zinc pyrithione, zinc pyrithione solution, sorbic acid, potassium sorbate, thianthol, thioxolone, thimol; thiram, dehydroacetic acid, sodium dehydroacetate, trichlorocarbanilide, trichlorohydroxydiphenyl ether, isobutyl paraoxybenzoate, isopropyl paraoxybenzoate, ethyl paraoxybenzoate, butyl paraoxybenzoate, propyl paraoxybenzoate, benzyl paraoxybenzoate, methyl paraoxybenzoate, sodium methyl paraoxybenzoate, parachlorphenol, sodium paraphenolsulfonate (dihydrate), halocarban, phenoxyethanol, phenol, hexachlorophane, mononitroguaiacol, mononitroguaiacol sodium, paradimethylaminostyrylheptylmethyl lyazolinium iodide, lauryltrimethylammonium trichlorophenoxide, oxyquinoline sulfate, oxyquinoline phosphate, and resorcin.

Adding and mixing the following various raw materials with the cosmetic raw material allows for obtaining skin cosmetic products that exhibit excellent compatibility with the skin and can impart it with superior moisture and smoothness. The various raw materials that can be used in the skin cosmetic products are exemplified by the above-described nonionic surfactants, pH adjusters, antiseptics, antifungal agents, antirust agents, etc., and, in addition to them, by oils and fats, such as avocado oil, almond oil, olive oil, cacao butter, sesame oil, wheat germ oil, safflower oil, shea butter, turtle oil, tung oil, persic oil, sunflower oil, grapeseed oil, macadamia nut oil, mink oil, egg yolk oil, Japan tallow, coconut oil, rosehip oil, and hardened oil; waxes, such as orange roughy oil, carnauba wax, candelilla wax, whale wax, jojoba oil, montan wax, beeswax, and lanolin; hydrocarbons, such as liquid paraffin, Vaseline, paraffin, ceresin, microcrystalline wax, and squalane; higher fatty acids, such as lauric acid, myristic acid, palmitic acid, stearic acid, oleic acid, behenic acid, undecylenic acid, oxystearic acid, linoleic acid, lanolic acid, and synthetic fatty acids; alcohols, such as ethyl alcohol, isopropyl alcohol, lauryl alcohol, cetyl alcohol, cetostearyl alcohol, stearyl alcohol, oleyl alcohol, behenyl alcohol, lanolin alcohol; hydrogenated lanolin, alcohol, hexyldecanol, octyldodecanol, and isostearyl alcohol; sterols, such as cholesterol, dihydrocholesterol, and phytosterol; fatty acid esters, such as ethyl linoleate, isopropyl myristate, lanolin fatty acid isopropyl, hexyl laurate, myristyl myristate, cetyl myristate, octyldodecyl myristate, decyl oleate, octyldodecyl oleate, hexyldecyl dimethyloctanoate, cetyl isooctanoate, cetyl palmitate, glycerin trimyristate, glycerin tri(capryl-caprate), propylene glycol dioleate, glycerin triisostearate, glycerin triisooctanoate, cetyl lactate, myristyl lactate, and diisostearyl malate; humectants, such as glycerin, propylene glycol, 1,3-butylene glycol, polyethylene glycol, sodium d,l-pyrrolidonecarboxylate, sodium lactate, sorbitol, and sodium hyaluronate; cationic surfactants; amphoteric surfactants, such as betain-type, amino acid-type, imidazoline-type, and lecithin; iron oxides and other colored pigments, zinc oxide, titanium oxide, zirconium oxide, and other white pigments; mica, talc, sericite, and other skin-color pigments; silicone oils, such as dimethylpolysiloxane, methylphenylpolysiloxane, octamethylcyclotetrasiloxane, decamethylcyclopentasiloxane, polyether-modified silicone oil, and amino-modified silicone oil; demineralized water; thickeners, such as carrageenan, alginic acid, gum arabic, traganth, pectin, starch, xanthan gum, polyvinyl alcohol, polyvinyl pyrrolidone, sodium polyacrylate, and polyethylene glycol; film-forming agents, such as silicone-acrylic copolymer, silicone resin, and acrylic polymers; and, furthermore, UV absorbers, antibacterial agents, anti-inflammatory agents, anti-perspirant agents, fragrance, anti-oxidants, and propellants. In addition, hand creams, skin creams, foundation, eye shadow, face wash, and body shampoo are specifically mentioned as the skin cosmetic products.

In addition, when the cosmetic raw material is used in a hair-care cosmetic product, in addition to the above-described anionic surfactants, nonionic surfactants, pH adjusters, antiseptics, antifungal agents, and antirust agents, compounding it with various raw materials such as film-forming agents, anti-freezing agents, oily components, emulsifiers, wetting agents, anti-dandruff agents, anti-oxidants, chelating agents, UV absorbers, fragrances, and colorants makes it possible to obtain hair-care cosmetic products that exhibit excellent adhesion to hair and are capable of imparting it with superior moisture and smoothness. Specifically, the film forming agents are exemplified by polymers of (meth) acrylic radical-polymerizable monomers and their copolymers with silicone compounds, poly(N-acylalkyleneimine), poly(N-methylpyrrolidone), silicone resins modified by fluorine-containing organic groups or amino groups, and non-functional silicone resins.

Further, as the hair cosmetic products, higher alkyl modified silicone, alkyl modified silicone resin and polyamide modified silicone resin which are particularly preferable as organic modified silicone can also be used as a base material of oily solid hair cosmetic products. In addition, higher organic alcohols, hydrocarbon oils, fatty acid ester oils, higher fatty acids, oils and fats, and fluorine oils can be used as the organic oil agent. These oil agents exhibit excellent compatibility and dispersibility, for example, with respect to sugar alcohol-modified silicones, so that they can be stably incorporated into the hair cosmetic products of the present invention, and when sugar alcohol-modified silicone is used, its effect can reinforce the peculiar effects of each.

Further, as the oil agent, a silicone oil agent and a non-silicone oil agent may be used in combination. By using both in combination, in addition to the refreshing feel peculiar to the silicone oil, the hair cosmetic products of the present invention can hold moisture of the hair and can impart a moisturizing sensation (also referred to as "moist feel") or a smooth feeling so that the hair moistens, and there is an advantage that the stability with time of the cosmetic products is not impaired. In addition to the above-mentioned oils, fats and oils, higher fatty acids, fluorine-containing oils and the like may be used as an oil agent, and two or more of these may be used in combination. In particular, vegetable-derived fats and oils are preferably used for the hair cosmetic products of the present invention because they give a healthy image derived from natural products and are superior in moisture retention, good for familiarity with hair and the like. The blending amount of the oil agent in the hair cosmetic of the present invention is not particularly limited, but it is preferably in the range of 0.1 to 90% by weight (mass), more preferably 0.5 to 70% by weight (mass), still more preferably 1 to 50% by weight (mass), particularly preferably 5 to 25% by weight (mass).

[Water Soluble Polymer]

The hair cosmetic product of the present invention preferably contains a water-soluble polymer. The water-soluble polymer is blended for the purpose of preparing a hair cosmetic product of a desired dosage form and improving feel of use of the hair cosmetic product such as feeling on the hair etc. and improvement of the conditioning effect.

As the water-soluble polymer, any amphoteric, cationic, anionic, nonionic, water-swellable clay mineral can be used as long as it is used in ordinary hair cosmetic products, and one or two or more kinds of water-soluble polymers can be used in combination. These water-soluble polymers have a thickening effect on water-containing components, and therefore are particularly useful when obtaining gel-like hydrated hair cosmetic products, water-in-oil emulsion hair cosmetic products, and oil-in-water type emulsion hair cosmetic products.

Examples of natural water-soluble polymers include vegetable polymers (e.g. gum arabic, tragacanth gum, galactan, guar gum, carob gum, karaya gum, carrageenan, pectin, agar, quince seed (marmelo: Cydonia oblonga), alga colloid (brown alga extract), starch (rice, corn, potato, wheat), glycyrrhizic acid, etc.), microbial polymers (e.g. xanthan gum, dextran, succinoglucan, pullulan, etc.), and animal polymers (e.g. collagen, casein, albumin, gelatin, etc.). Examples of the semi-synthetic water-soluble polymer include starch-based polymers (e.g. carboxymethylstarch, methylhydroxypropylstarch, etc.), cellulose-based polymers (e.g. methylcellulose, nitrocellulose, ethylcellulose, methylhydroxypropylcellulose, hydroxyethylcellulose, sodium cellulose sulfate, hydroxypropyl cellulose, sodium carboxymethylcellulose (CMC), crystalline cellulose, cellulose powder, etc.), alginic acid-based polymers (e.g. sodium alginate, propylene glycol alginate ester, etc.). Examples of the synthetic water-soluble polymer include vinyl-based polymers (e.g. polyvinyl alcohol, polyvinyl methyl ether polymer, polyvinyl pyrrolidone, carboxy vinyl polymer (CARBOPOL 940, 941; Lubrizol Japan Ltd.), polyoxyethylene-based polymers (e.g. polyethylene glycol 20,000, polyethylene glycol 6,000, polyethylene glycol 4,000, etc.), copolymer-based polymers (e.g. polyoxyethylene-polyoxypropylene copolymer, PEG/PPG methyl ether, etc.), acrylic polymers (e.g. sodium polyacrylate, poly ethyl acrylate, polyacrylamide, etc.), polyethylene imine, cationic polymers and the like. The water-swellable clay mineral is an inorganic water-soluble polymer and is one type of colloid-containing aluminum silicate having a three-layer structure, and specifically includes bentonite, montmorillonite, beidellite, nontronite, saponite, hectorite, magnesium aluminum silicate, and silicic acid anhydride, and these may be either natural products or synthetic products.

Particularly cationic water-soluble polymers can be mentioned as components that can be suitably blended in the hair cosmetic products. Specific examples of the cationic water-soluble polymer include quaternary nitrogen-modified polysaccharides (e.g. cation modified cellulose, cation modified hydroxyethyl cellulose, cation modified guar gum, cation modified locust bean gum, cation modified starch, etc.), dimethyldiallyl derivative ammonium chloride (e.g. dimethyldiallyl ammonium chloride/acrylamide copolymer, polychlorinated dimethylmethylene piperidinium, etc.), a vinylpyrrolidone derivatives (e.g. vinylpyrrolidone/dimethylaminoethyl methacrylic acid copolymer salt, vinylpyrrolidone/methacrylamide propyltrimethyl ammonium chloride copolymer, vinylpyrrolidone/methylvinyl imidazolium chloride copolymer, etc.), methacrylic acid derivatives (e.g. methacryloyl ethyl dimethyl betaine/methacryloyl ethyl trimethyl ammonium chloride/2-hydroxyethyl methacrylate copolymer, methacryloyl ethyl dimethyl betaine/methacryloyl ethyl trimethyl ammonium chloride/methoxy polyethylene glycol methacrylate copolymer, etc.).

In addition, amphoteric water-soluble polymers can be mentioned as components that can be suitably blended in hair cosmetic products. Specific examples of the amphoteric water-soluble polymer include amphoteric starch, dimethyldiallyl ammonium chloride derivatives (e.g. acrylamide/acrylic acid/dimethyldiallyl ammonium chloride copolymer, acrylic acid/dimethyldiallyl ammonium chloride copolymer), methacrylic acid derivatives (e.g. polymethacryloyl ethyl dimethyl betaine, (methacryloyloxyethyl carboxybetaine/alkyl methacrylate) copolymer, (octyl acrylamide/hydroxypropyl acrylate/butylaminoethyl methacrylate) copolymer, N-methacryloyloxyethyl N,N-dimethylammonium-α-methylcarboxybetaine/alkyl methacrylate copolymer.

The blending amount of the water-soluble polymer in the hair cosmetic products of the present invention can be appropriately selected depending on the type and purpose of the cosmetic products, but it is preferably in the range of 0.01 to 5.0% by weight (mass) with respect to the hair cosmetic products, more preferably in the range of 0.1 to 3.0% by weight (mass) to obtain a particularly good feeling of use.

When the blending amount of the water-soluble polymer exceeds the upper limit, depending on the type of hair cosmetic products, there may be cases where a rough and stiff feeling remains on the hair, and if the blending amount of the water-soluble polymer is less than the lower limit, advantageous technical effects such as thickening effect and conditioning effect may not be sufficiently achieved in some cases.

[Alcohols]

It is preferable that the hair cosmetic product of the present invention further includes alcohols in addition to the alcohol used in the polyorganosiloxane emulsion polymerization. As the alcohols, one or two or more polyhydric alcohols and/or monohydric lower alcohols can be used. As the lower alcohols, ethanol, isopropanol, n-propanol, t-butanol, sec-butanol and the like are exemplified, and ethanol is preferable. Examples of the polyhydric alcohol may include dihydric alcohols such as 1,3-propanediol, 1,3-butylene glycol, 1,2-butylene glycol, propylene glycol, trimethylene glycol, tetramethylene glycol, 2,3-butylene glycol, pentamethylene glycol, 2-butene-1,4-diol, dibutylene glycol, pentyl glycol, hexylene glycol, and octylene glycol, trihydric alcohols such as glycerin, trimethylolpropane, and 1,2,6-hexanetriol, 4-or-more-valent polyhydric alcohols such as pentaerythritol and xylitol, and sugar alcohols such as sorbitol, mannitol, maltitol, maltotriose, sucrose, erythritol, glucose, fructose, starch decomposition product, maltose, xylitose, and starch degradation sugar reducing alcohol. In addition to these low molecular polyhydric alcohols, polyhydric alcohol polymers such as diethylene glycol, dipropylene glycol, triethylene glycol, polypropylene glycol, tetraethylene glycol, diglycerin, polyethylene glycol, triglycerin, tetraglycerin, and polyglycerin are exemplified. Among those, 1,3-propanediol, 1,3-butylene glycol, sorbitol, dipropylene glycol, glycerin, and polyethylene glycol are particularly preferable.

The blending amount of the alcohols is preferably in the range of 0.1 to 50% by weight (mass) with respect to the total hair cosmetic product. The alcohols can be blended in an amount of about 5 to 30% by weight (mass) with respect to the total hair cosmetic product for the purpose of improving the preservation stability of the hair cosmetic product, which is a preferred embodiment of the present invention.

[Thickener/Gelling Agent]

It is preferable that the hair cosmetic product of the present invention further includes a thickener/gelling agent. Although as the water-based thickener/gelling agent, the above-mentioned water-soluble polymer is preferably used, examples of an oil-soluble thickener/gelling agent may include metallic soaps such as aluminum stearate, magnesium stearate, and zinc myristate, amino acid derivatives such as N-lauroyl-L-glutamic acid, and α,γ-di-n-butylamine, dextrin fatty acid esters such as dextrin palmitate ester, dextrin stearate ester, and dextrin 2-ethylhexanoate palmitate ester, sucrose fatty acid esters such as sucrose palmitate ester and sucrose stearate ester, benzylidene derivatives of sorbitol such as monobenzylidene sorbitol, and dibenzylidene sorbitol, and the like. These can be used alone or in combination of two or more, if necessary.

Organically modified clay minerals may be used as the thickener/gelling agent. Like the oil-soluble thickener/gelling agent, the organically modified clay mineral can be used as a thickener/gelling agent for an oil agent. Examples of the organically modified clay mineral may include dimethylbenzyldodecylammonium montmorillonite clay, dimethyldioctadecylammonium montmorillonite clay, dimethylalkylammonium hectorite, benzyldimethylstearylammonium hectorite, distearyldimethylammonium chloride treated magnesium aluminum silicate, and the like. Examples of these commercially available products may include Bentone 27 (benzyldimethylstearylammonium chloride treated hectorite: manufactured by National Red Co.), Bentone 38 (distearyldimethylammonium chloride treated hectorite: manufactured by National Red Co.), and the like.

The amount of the thickener/gelling agent used in the hair cosmetic product of the present invention is not particularly limited, but it is preferably in the range of 0.5 to 50 parts by weight (mass) with respect to 100 parts by weight (mass) of the oil agent, and more preferably in the range of 1 to 30 parts by weight (mass). The proportion of the thickener/gelling agent with respect to the total hair cosmetic product is preferably 0.01 to 30% by weight (mass). The proportion of the thickener/gelling agent with respect to the total hair cosmetic product is more preferably 0.1 to 20% by weight (mass), and still more preferably 1 to 10% by weight (mass).

It is possible to properly adjust the viscosity and hardness of the cosmetic product, improve the appearance, compatibility, and use feeling of the cosmetic product, and be carried out in the desired dosage form/cosmetic product form, by thickening or gelling the oil agent in the hair cosmetic product of the present invention. If the thickener/gelling agent are used, there is a quality advantage that the oiliness (greasy sticky feeling) is further suppressed on the whole and the hair retention can be further improved.

[Powder]

The hair cosmetic product of the present invention may further include powder. The "powder" of the present invention is generally used as a component of a cosmetic product, and includes white and colored pigments and extender pigments. The white and colored pigments are used for the coloring of the cosmetic product and the like, whereas the extender pigments are used for improving the feeling of the cosmetic product and the like. As the powder in the present invention, the white and colored pigments and the extender pigments commonly used in the cosmetic product can be used without any particular limitation. It is preferable to blend one or two or more powders.

Although the shape (spherical shape, rod shape, needle shape, tabular shape, irregular shape, spindle shape and the like), particle diameter (fumed shape, fine particles, pigment grade and the like) and particle structure (porous and non-porous) of the powder is not limited at all, the average primary particle diameter is preferably in the range of 1 nm to 100 μm.

Examples of the powder may include inorganic powder, organic powder, surfactant metal salt powder (metallic soap), colored pigment, pearl pigment, metal powder pigment, and the like, and a combination thereof can also be used. Specific examples of the inorganic powder may include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, lepidolite, biotite, lithia mica, silicic acid, anhydrous silicic acid, aluminum silicate, sodium silicate, sodium magnesium silicate, magnesium silicate, aluminum magnesium silicate, calcium silicate, barium silicate, strontium silicate, tungstate metal salt, hydroxyapatite, vermiculite, hydrargilite, bentonite, montmorillonite, hectorite, zeolite, ceramics powder, dibasic calcium phosphate, alumina, aluminum hydroxide, boron nitride, and the like; specific examples of the organic powder may include polyamide powder, polyester powder, polyethylene powder, polypropylene powder, polystyrene powder, polyurethane powder, benzoguanamine powder, polymethylbenzoguanamine powder, polytetrafluoroethylene powder, polymethyl methacrylate powder, cellulose, silk powder, nylon powder, 12 nylon, 6 nylon, silicone powder, polymethylsilsesquioxane spherical powder, a styrene/acrylic acid copolymer, a divinylbenzene/styrene copolymer, a vinyl resin, an urea resin, a phenol resin, a fluororesin, a silicone resin, an acrylic resin, a melamine resin, an epoxy resin, a polycarbonate resin, microcrystalline fiber powder, starch powder, lauroyl lysine, and the like; examples of the surfactant metal salt powder may include zinc stearate, aluminum stearate, calcium stearate, magnesium stearate, zinc myristate, magnesium myristate, zinc palmitate, zinc laurate, zinc cetyl phosphate, calcium cetyl phosphate, sodium zinc cetyl phosphate, and the like; examples of the colored pigment may include inorganic red pigments of red oxide, iron oxide, iron hydroxide, and iron titanate, inorganic brown pigments such as γ-iron oxide, inorganic yellow pigments such as yellow iron oxide and yellow soil, inorganic black pigments such as black iron oxide and carbon black, inorganic violet pigments such as manganese violet and cobalt violet, inorganic green pigments such as chromium hydroxide, chromium oxide, cobalt oxide, and cobalt titanate, inorganic blue pigments such as iron blue and ultramarine blue, ones obtained by flaking tar-based dyes such as red No. 3, red No. 104, red No. 106, red No. 201, red No. 202, red No. 204, red No. 205, red No. 220, red No. 226, red No. 227, red No. 228, red No. 230, red No. 401, red No. 505, yellow No. 4, yellow No. 5, yellow No. 202, yellow No. 203, yellow No. 204, yellow No. 401, blue No. 1, blue No. 2, blue No. 201, blue No. 404, green No. 3, green No. 201, green No. 204, green No. 205, orange No. 201, orange No. 203, orange No. 204, orange No. 206, and orange No. 207, ones obtained by flaking natural pigments such as carminic acid, laccaic acid, carthamin, and brazilin, and the like; examples of the pearl pigment may include titanium oxide-coated mica, titanated mica, iron oxide-treated titanated mica, titanium oxide-coated mica, bismuth oxychloride, titanium oxide-coated bismuth oxychloride, titanium oxide-coated talc, fish scale flake, titanium oxide-coated colored mica, and the like; and examples of the metal powder pigment may include metal powder such as aluminum, gold, silver, copper, platinum, and stainless steel.

Further, it is particularly preferable that some or all of these powders are subjected to a surface treatment such as a water repellent treatment and a hydrophilic treatment. It should be noted that these powders may be combined with each other. It is also possible to carry out the surface treatment with a general oil agent, a silicone compound other than a sugar alcohol-modified silicone, a fluorine compound, a surfactant, a thickener and the like, and one or two or more thereof can be used.

The water repellent treatment is not particularly limited but it is possible to treat powder with various water repellent surface treatment agents. Examples of the water repellent treatment may include an organosiloxane treatment such as a methyl hydrogen polysiloxane treatment, a silicone resin treatment, a silicone gum treatment, an acrylic silicone treatment, and a fluorinated silicone treatment; a metallic soap treatment such as a zinc stearate treatment; a silane treatment such as a silane coupling agent treatment and an alkylsilane treatment; a fluorine compound treatment such as perfluoroalkylsilane, perfluoroalkylphosphate ester salt, and perfluoropolyether treatment; an amino acid treatment such as an N-lauroyl-L-lysine treatment; an oil agent treatment such as a squalane treatment; an acrylic treatment such as an alkyl acrylate treatment, and the like, and combinations of two or more selected therefrom can be used.

It is also possible to use silicone elastomer powder as powder. The silicone elastomer powder is a crosslinked product of a straight-chain diorganopolysiloxane mainly composed of diorganosiloxy units (D units), and can be properly obtained by performing a cross-linking reaction on organohydrogenpolysiloxane having a silicon-bonded hydrogen atom at the side chain or the terminal and diorganopolysiloxane having an unsaturated hydrocarbon group such as an alkenyl group at the side chain or the terminal under a hydrosilylation reaction catalyst. The silicone elastomer powder is softer, more elastic and excellent in oil absorbability as compared with silicone resin powder containing a T unit and a Q unit, so it can absorb oils and fats on the skin and prevent makeup collapse.

The blending amount of the powder in the hair cosmetic product of the present invention is not particularly limited, but it preferably ranges from 0.1 to 50% by weight (mass) with respect to the total cosmetic product, more preferably ranges from 1 to 30% by weight (mass), and still more preferably ranges from 5 to 15% by weight (mass).

[Solid Silicone Resin or Crosslinking Organopolysiloxane]

The hair cosmetic product of the present invention may further include a solid silicone resin or a crosslinking organopolysiloxane. It is preferred that the solid silicone resin or the crosslinking organopolysiloxane has hydrophobicity so that it is not completely dissolved in water at room temperature or the solubility of the component in 100 g of water is less than 1% by weight (mass).

The solid silicone resin is the organopolysiloxane having a highly branched structure, a network structure or a cage structure and is solid at room temperature. Any silicone resin usually used in the hair cosmetic product can be used so long as it is not contrary to the object of the present invention. The solid silicone resin may be particles such as a spherical powder, a flake-like powder, a needle-like powder, and a flat flake-like powder (including a tabular powder having an appearance generally understood as a plate shape and an aspect ratio of particles). In particular, the silicone resin powder containing a monoorganosiloxy unit (T unit) and/or a siloxy unit (Q unit) to be described later is preferably used.

One or two or more of the solid silicone resin or the crosslinking organopolysiloxane may be blended according to the purpose, and the blending is preferably made in the range of 0.05 to 25% by weight (mass) with respect to the total hair cosmetic product, and is more preferably made in the range of 0.1 to 15% by weight (mass) according to the purpose and blending intention.

[Acrylic Silicone Dendrimer Copolymer]

The hair cosmetic product of the present invention may further include an acrylic silicone dendrimer copolymer. The acrylic silicone dendrimer copolymer is a vinyl polymer having a carbosiloxane dendrimer structure at the side chain. For example, the vinyl polymer described in Japanese Patent No. 4009382 (JP 2000-063225 A) is particularly preferably exemplified. Examples of commercially available products may include FA 4001 CMS Silicone Acrylate and FA 4002 ID Silicone Acrylate manufactured by Dow Corning Toray Co., Ltd., but an acrylic silicone dendrimer copolymer having a long chain alkyl group having 8 to 30 carbon atoms, preferably 14 to 22 carbon atoms at the side chain or the like may be used.

When the acrylic silicone dendrimer copolymer is blended alone, since it has excellent film-forming properties, it is blended in the hair cosmetic product of the present invention, such that it is possible to form a firm coating film on the coated portion and improve durability such as sebum resistance or abrasion resistance.

The blending amount of the acrylic silicone dendrimer copolymer is appropriately selected according to the purpose and the blending intention, but is preferably in the range of 1 to 99% by weight (mass) with respect to the total hair cosmetic product, and more preferably in the range of 30 to 70% by weight (mass).

[Ultraviolet Protection Component]

The hair cosmetic product of the present invention may further include an ultraviolet protecting component. It is preferred that the ultraviolet protecting component has hydrophobicity so that it is not completely dissolved in water at room temperature or the solubility of the component in 100 g of water is less than 1 weight (mass) %. The ultraviolet protecting component is a component that shields or scatters ultraviolet rays, and includes an inorganic ultraviolet protecting component and an organic ultraviolet protecting component. If the hair cosmetic product of the present invention should has a sunscreen effect, it is preferable to contain at least one kind of inorganic or organic ultraviolet protecting component, particularly, an organic ultraviolet protecting component.

The inorganic ultraviolet protecting component may be one in which the inorganic pigment powder, the metal powder pigment and the like are blended as an ultraviolet scattering agent, and may include metal oxides such as titanium oxide, zinc oxide, cerium oxide, low order titanium oxide, and iron-doped titanium oxide, metal hydroxides such as iron hydroxide, metal flakes such as tabular iron oxide and aluminum flakes, and ceramics such as silicon carbide. Among them, at least one kind selected from fine particle metal oxides and fine particle metal hydroxides having an average particle diameter of 1 to 100 nm and a granular, tabular, acicular or fibrous form is particularly preferable. These powders are preferably subjected to the conventionally known surface treatments, for example, the fluorine compound treatment (perfluoroalkyl phosphate treatment, perfluoroalkyl silane treatment, perfluoropolyether treatment, fluorosilicone treatment, or fluorinated silicone resin treatment is preferable), the silicone treatment (methylhydrogenpolysiloxane treatment, dimethylpolysiloxane treatment, or gas phase method tetramethyltetrahydrogen cyclotetrasiloxane treatment is preferable), a silicone resin treatment (trimethylsiloxysilicic acid treatment is preferable), a pendant treatment (method of adding alkyl chain or the like after gas phase method silicone treatment), a silane coupling agent treatment, a titanium coupling agent treatment, a silane treatment (alkylsilane or alkylsilazane treatment is preferable), an oil agent treatment, an N-acylated lysine treatment, a polyacrylic acid treatment, a metallic soap treatment (stearic acid or myristate is preferable), an acrylic resin treatment, a metal oxide treatment, and the like, and it is preferable that these treatments are performed in plural. For example, the surface of the fine particulate titanium oxide is coated with the metal oxides such as silicon oxide and alumina, and is then subjected to the surface treatment with alkylsilane or the like. It is preferable that the surface treatment amount is preferably in the range of 0.1 to 50% by weight (mass) with respect to the total powder.

The organic ultraviolet protecting component has generally lipophobicity and may include benzoic acid-based ultraviolet absorbents such as paraaminobenzoic acid (hereinafter, abbreviated as PABA), PABA monoglycerin ester, N,N-dipropoxy PABA ethyl ester, N,N-diethoxy PABA ethyl ester, N, N-dimethyl PABA ethyl ester, N, N-dimethyl PABA butyl ester, and 2-[4-(diethylamino)-2-hydroxybenzoyl] benzoic acid hexyl ester (trade name: Uvinul A plus), anthranilic acid-based ultraviolet absorbents such as homomenthyl-N-acetyl anthranilate, salicylic acid-based ultraviolet absorbents such as amyl salicylate, menthyl salicylate, homomenthyl salicylate, octyl salicylate, phenyl salicylate, benzyl salicylate, and p-isopropanol phenyl salicylate, cinnamic acid-based ultraviolet absorbents such as octyl cinnamate, ethyl 4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, glyceryl mono-2-ethylhexanoyl-diparamethoxy cinnamate, 3,4,5-trimethoxy cinnamic acid 3-methyl-4-[methylbis (trimethylsiloxy)silyl] butyl, and dimethicone ethyl benzalmalonate (trade name: Parsol SLX (INCI name: polysilicone-15)), benzophenone-based ultraviolet absorbents such as 2,4-dihydroxybenzophenone, 2,2'-dihydroxy-4-methoxybenzophenone, 2,2'-dihydroxy-4,4'-dimethoxybenzophenone, 2,2',4,4'-tetrahydoxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, hydroxy-4-n-octoxybenzophenone, and 4-hydroxy-3-carboxybenzophenone, benzotriazole-based ultraviolet absorbents such as 3-(4'-methylbenzylidene)-d,l-camphor, 3-benzylidene-d,l-camphor, urocanic acid, urocanic acid ethyl ester, 2-phenyl-5-methylbenzoxazole, 2,2'-hydroxy-5-methylphenylbenzotriazole, 2-(2'-hydroxy-5'-t-octylphenyl) benzotriazole, 2-(2'-hydroxy-5'-methylphenylbenzotriazole, dibenzalazine, dianisoylmethane, 4-methoxy-4'-t-butyldibenzoylmethane, 5-(3,3-dimethyl-2-norbornylidene)-3-pentan-2-one, and 2,2'-methylenebis(6-(2H-benzotriazol-2-yl)-4-(1,1,3,3-tetramethylbutyl)phenol) {trade name: trade mark Tinosorb M}, triazole-based ultraviolet absorbents such as 2,4,6-tris[4-(2-ethylhexyloxycarbonyl)anilino] 1,3,5-triazine {INCI: octyltriazone}, and 2,4-bis{([4-(2-ethyl-hexyloxy)-2-hydroxy]phenyl}-6-(4-methoxyphenyl)-1,3,5-triazine {INCI: bis-ethylhexyloxyphenol methoxyphenyl triazine, trade name: trade mark Tinosorb S}, 2-cyano-3,3-diphenylprop-2-enoic acid 2-ethylhexyl ester {INCI: octocrylene} and the like.

In addition, it is also possible to use one in which the organic ultraviolet protecting component is contained in the hydrophobic polymer powder. The polymer powder may or may not be hollow, the average primary particle diameter may be in the range of 0.1 to 50 μm, and the particle size distribution may be broad or sharp. Examples of the polymer may include an acrylic resin, a methacrylic resin, a styrene resin, a polyurethane resin, polyethylene, polypropylene, polyethylene terephthalate, a silicone resin, nylon, acrylamide resin, and a silylated polypeptide resin.

A polymer powder containing an organic ultraviolet protecting component in the range of 0.1 to 30 weight (mass) % is preferable, and in particular, a polymer powder containing 4-tert-butyl-4'-methoxydibenzoylmethane that is an UV-A absorbent is preferable.

In the hair cosmetic product of the present invention, the ultraviolet protecting component which can be preferably used are at least one selected from the group consisting of fine particle titanium oxide, fine particle zinc oxide, 2-ethylhexyl paramethoxy cinnamate, 4-tert-butyl-4'-methoxydibenzoylmethane, a benzotriazole-based ultraviolet absorbent, and a triazine-based ultraviolet absorbent.

These (J) ultraviolet protecting components can be widely used, easily obtained, and appropriately used to increase the ultraviolet protection effect. In particular, it is preferable to use the inorganic and organic ultraviolet protecting components in combination, and it is more preferable to use an ultraviolet protecting component corresponding to UV-A and an ultraviolet protecting component corresponding to UV-B in combination.

In the hair cosmetic product of the present invention, it is possible to stably disperse the ultraviolet protecting component in the cosmetic product while improving the feeling and preservation stability of the entire cosmetic product by using the sugar alcohol-modified silicone and the ultraviolet protecting component in combination, and as a result it is possible to impart the excellent ultraviolet protection function to the cosmetic product.

In the hair cosmetic product of the present invention, it is preferable to blend the ultraviolet protecting component in a total amount of 0.1 to 40.0 weight (mass) % with respect to the total cosmetic product, more preferably 0.5 to 15.0 weight (mass) %.

[Oxidation Dye]

When the hair cosmetic product of the present invention is used as an oxidation hair dye, the hair cosmetic product of the present invention may contain (K) oxidation dye. As the oxidation dyes, those commonly used for the oxidation hair dye such as an oxidation dye precursor and a coupler can be used. Examples of the oxidation dye precursor may include phenylenediamines, aminophenols, diaminopyridines, salts such as hydrochloride and sulfate thereof, and the like. Specific examples thereof may include phenylenediamines such as p-phenylenediamine, toluene-2,5-diamine, toluene-3,4-diamine, 2,5-diaminoanisole, N-phenyl-p-phenylenediamine, N-methyl-p-phenylenediamine, N,N-dimethyl-p-phenylenediamine, 6-methoxy-3-methyl-p-phenylenediamine, N,N-diethyl-2-methyl-p-phenylenediamine, N-ethyl-N-(hydroxyethyl)-p-phenylenediamine, N-(2-hydroxypropyl)-p-phenylenediamine, 2-chloro-6-methyl-p-phenylenediamine, 2-chloro-p-phenylenediamine, N,N-bis-(2-hydroxyethyl)-p-phenylenediamine, 2,6-dichloro-p-phenylenediamine, and 2-chloro-6-bromo-p-phenylenediamine; aminophenols such as p-aminophenol, o-aminophenol, 2,4-diaminophenol, 5-aminosalicylic acid, 2-methyl-4-aminophenol, 3-methyl-4-aminophenol, 2,6-dimethyl-4-aminophenol, 3,5-dimethyl-4-aminophenol, 2,3-dimethyl-4-aminophenol, 2,5-dimethyl-4-aminophenol, 2-chloro-4-aminophenol, 3-chloro-4-aminophenol; diaminopyridines such as 2,5-diaminopyridine, and salts thereof, and the like. In addition, as the coupler, resorcin, m-aminophenol, m-phenylenediamine, 2,4-diaminophenoxyethanol, 5-amino-o-cresol, 2-methyl-5-hydroxyethylaminophenol, 2,6-diaminopyridine, catechol, pyrogallol, gallic acid, tannic acid and the like, and salts thereof can be used. In addition, those listed in "Japanese Standards of Quasi-drug Ingredients" (issued June 1991, Yakuji Nippo Limited) can also be used as appropriate. Further, one of these oxidation dye precursors and couplers can be used alone or two or more thereof can be used in combination, and it is preferable to use at least the oxidation dye precursor. The content of the oxidation dye is preferably about 0.01 to 10% by weight in the hair cosmetic product from the viewpoints of hair dyeing properties and safety such as skin irritation.

When the hair cosmetic product of the present invention is used as a two-agent type oxidation hair dye, an alkalizing agent and an oxidation dye (preferably, a coupler) are contained in a first agent and an oxidizing agent is contained in a second agent, in which the first agent and the second agent may be generally mixed at a ratio of 1:5 to 5:1 in use.

When the hair cosmetic product of the present invention is used as a hair-bleaching agent, the hair cosmetic product of the present invention may contain the oxidizing agent. When the hair cosmetic product of the present invention is used as a two-agent type bleaching agent, an alkalizing agent is contained in a first agent and an oxidizing agent is contained in a second agent, in which the first agent and the second agent may be generally mixed at a ratio of 1:5 to 5:1 in use.

[Direct Dye]

When the hair cosmetic product of the present invention is used as a temporary hair dye (for example, hair manicure) of hair, the hair cosmetic product of the present invention can contain direct dyes. Examples of the direct dye may include nitro dyes, anthraquinone dyes, acid dyes, oil-soluble dyes, basic dyes and the like. Examples of the nitro dye may include HC blue 2, HC orange 1, HC red 1, HC red 3, HC yellow 2, HC yellow 4, and the like. Examples of the anthraquinone dye include 1-amino-4-methylaminoanthraquinone, 1,4-diaminoanthraquinone and the like. Examples of the acidic dye may include red No. 2, red No. 3, red No. 102, red No. 104, red No. 105, red No. 106, red No. 201, red No. 227, red No. 230, red No. 232, red No. 401, red No. 502, red No. 503, red No. 504, red No. 506, orange No. 205, orange No. 206, orange No. 207, yellow No. 4, yellow No. 5, yellow No. 202, yellow No. 203, yellow No. 402, yellow No. 403, yellow No. 406, yellow No. 407, green No. 3, green No. 201, green No. 204, green No. 205, green No. 401, green No. 402, blue No. 1, blue No. 2, blue No. 202, blue No. 205, violet No. 401, black No. 401, acid blue 1, acid blue 3, acid blue 62, acid black 52, acid brown 13, acid green 50, acid orange 6, acid red 14, acid red 35, acid red 73, acid red 184, brilliant black 1, and the like. Examples of the oil-soluble dye may include red No. 215, red No. 218, red No. 225, orange No. 201, orange No. 206, yellow No. 201, yellow No. 204, green No. 202, violet No. 201, red No. 501, red No. 505, orange No. 403, yellow No. 404, yellow No. 405, blue No. 403 and the like, and the oil-soluble dyes may be used for, for example, color rinse, a color treatment and the like. Examples of the basic dye may include basic blue 6, basic blue 7, basic blue 9, basic blue 26, basic blue 41, basic blue 99, basic brown 4, basic brown 16, basic brown 17, basic green 1, basic red 2, basic red 12, basic red 22, basic red 51, basic red 76, basic violet 1, basic violet 3, basic violet 10, basic violet 14, basic violet 57, basic yellow 57, basic yellow 87, basic orange 31 and the like. Among those, preferable examples of the acid dye may include, in particular, yellow No. 4, yellow No. 203, yellow No. 403, orange No. 205, green No. 3, green No. 201, green No. 204, red No. 2, red No. 104, red No. 106, red No. 201, red No. 227, blue No. 1, blue No. 205, violet No. 401, and black No. 401. One or more of (L) direct dye can be used, and the blending amount thereof in the hair cosmetic product of the present invention is not particularly limited but preferably ranges from 0.005 to 5% by weight, more preferably 0.01 to 2% by weight with respect to the total weight of the hair cosmetic product.

When the hair cosmetic product of the present invention is used as a permanent agent, the hair cosmetic product of the present invention may contain the reducing agent and the oxidizing agent. When the hair cosmetic composition of the present invention is used as a two-agent type permanent agent, for example, the reducing agent (preferably, an alkalizing agent) is contained in the first agent and the oxidizing agent is contained in the second agent. First, a disulfide bond of hair is dissociated using the first agent, and then a hairstyle may be arranged to the desired shape, and the disulfide bond of the hair using the second agent may also be regenerated to fix the hair style.

[Other Components]

The hair cosmetic product of the present invention may further contain other components usually used in hair cosmetic products so long as the effects of the present invention are not hindered. For example, a refrigerant, an anti-inflammatory agent, a physiologically active component (whitening agent, cell activator, chapped skin-improving agent, blood circulation promoting agent, skin astringent, antiseborrheic agent and the like), vitamins, amino acids, nucleic acids, hormones, clathrate compounds, natural plant extract components, seaweed extract components, herbal medicine components, water, a volatile solvent and the like can be added to the hair cosmetic product. Other components are not particularly limited. These may be used alone or in combination of two or more.

Examples of the organic resin may include polyvinyl alcohol, polyvinyl pyrrolidone, an alkyl polyacrylate copolymer, and the like. Since the organic resin has excellent film-forming properties, it is blended in the hair cosmetic product according to the present invention, such that it is possible to form a firm coating film on the coated portion, and improve the durability such as the sebum resistance and the abrasion resistance.

Examples of the moisturizing agent include hyaluronic acid, chondroitin sulfate, pyrrolidone carboxylate, polyoxyethylene methyl glucoside, polyoxypropylene methyl glucoside, and the like. It goes without saying that the above-mentioned polyhydric alcohols exert a moisturizing function on the skin or hair.

Examples of the antiseptic may include p-hydroxybenzoic acid alkyl ester, benzoic acid, sodium benozate, sorbic acid, potassium sorbate, phenoxyethanol, and the like, examples of the antibacterial agent may include isothiazolinone compounds such as benzoic acid, salicylic acid, carbolic acid, sorbic acid, p-hydroxybenzoic acid alkyl ester, p-chlorometacresol, hexachlorophene, benzalkonium chloride, chlorhexidine chloride, trichlorocarbanilide, triclosan, photosensitizer, 2-methyl-4-isothiazolin-3-one, 5-chloro-2-methyl-4-isothiazolin-3-one, and amine oxides such as dimethyllaurylamine oxide and dihydroxyethyl laurylamine oxide.

Examples of the antibacterial agent include a phenolic compound such as apolactoferrin and resorcin; antibacterial or bactericidal basic protein or peptide such as iturin-based peptide, surfactin-based peptide, protamine or a salt thereof (protamine sulfate or the like); polylysines such as ε-polylysine or a salt thereof, and the like; antibacterial metal compound which is a metal compound capable of generating a salt thereof, a silver ion, a copper ion or the like; and antibacterial enzymes such as protease, lipase, oxidoreductase, carbohydrase, transferase, and phytase, and the like.

Examples of the perfume may include perfumes extracted from flowers, seeds, leaves, roots and the like of various plants, perfumes extracted from seaweeds, perfumes (e.g., musk, incense) extracted from parts or secretions of animals, and artificially synthesized perfumes (e.g., menthol, musk, acetate ester, vanilla). The perfume is blended for imparting aroma and fragrance to the hair cosmetic product or for masking an unpleasant odor, the known perfume is appropriately selected, and the perfume can be blended in an appropriate amount depending on the dosage form of the hair cosmetic product.

Examples of the oxidizing agent may include hydrogen peroxide, urea peroxide, alkali metal bromate and the like. On the other hand, examples of the antioxidant may include tocopherol, butylhydroxyanisole, dibutylhydroxytoluene, phytic acid and the like. As the antioxidant, ascorbic acid and/or an ascorbic acid derivative may be used.

Examples of the usable ascorbic acid derivatives may include, for example, sodium ascorbate, potassium ascorbate, calcium ascorbate, ammonium ascorbate, erythorbic acid, sodium erythorbate, ascorbic acid-phosphate ester magnesium, ascorbyl citrate, ascorbyl acetate, ascorbyl tartrate, ascorbyl palmitate, ascorbyl stearate, ascorbyl glucoside and the like. In addition, as the antioxidant, the reducing agent may be used, and for example, sulfurous acid, bisulfite, thiosulfate, thiolactic acid, thioglycolic acid, L-cysteine, N-acetyl-L-cysteine and salts thereof may be used appropriately.

Examples of the pH adjuster may include lactic acid, citric acid, glycolic acid, succinic acid, tartaric acid, dl-malic acid, potassium carbonate, sodium bicarbonate, ammonium carbonate, ammonium hydrogen carbonate and the like. In addition, an inorganic alkalizing agent such as ammonia and an organic alkalizing agent such as isopropanolamine, monoethanolamine, diethanolamine, triethanolamine, 2-amino-2-methyl-1-propanolamine and the like can be used. The blending amount of the pH adjuster is not particularly limited, but is preferably 0.01% by weight to 20% by weight, more preferably 0.1% by weight to 10% by weight with respect to the total weight of the hair cosmetic product.

Examples of the chelating agent may include alanine, sodium edetate, sodium polyphosphate, sodium metaphosphate, phosphoric acid and the like.

Examples of the refrigerant may include I-menthol, camphor and the like.

Examples of the physiologically active component may include vitamins, amino acids, nucleic acids, hormones, natural plant extract components, seaweed extract components, herbal medicine components, placenta extraction liquid, whitening agents such as arbutin, glutathione and saxifrage extract, cell activators such as royal jelly, chapped skin-improving agent, blood circulation promoting agents such as nonylic acid varenylamide, nicotinic acid benzyl ester, nicotinic acid β-butoxyethyl ester, capsaicin, zingerone, cantharis tincture, ichthamol, caffeine, tannic acid, α-borneol, tocopherol nicotinate, inositol hexanicotinate, cyclandelate, cinnarizine, tolazoline, acetylcholine, verapamil, cepharanthine, and γ-oryzanol, skin astringents such as zinc oxide and tannic acid, antiseborrheic agents such as sulfur and thiantrol, anti-inflammatory agents such as such as ε-aminocaproic acid, glycyrrhizic acid, β-glycyrrhetinic acid, lysozyme chloride, guaiazulene, hydrocortisone, allantoin, tranexamic acid, and azulene, and the like Examples of the vitamins may include vitamin A group such as vitamin A oil, retinol, retinol acetate, and retinol palmitate, vitamin B2 group such as riboflavin, riboflavin butyrate, and flavin adenine nucleotide, vitamin B6 group such as pyridoxine hydrochloride, pyridoxine dioctanoate, and pyridoxine tripalmitate, vitamin B group such as vitamin B12 group and derivatives thereof and vitamin B15 group and derivatives thereof, vitamin C group such as L-ascorbic acid, L-ascorbic acid dipalmitc acid ester, sodium L-ascorbate-2-sulfate, and L-ascorbic acid phosphate diester dipotassium, vitamin D group such as ergocalciferol and cholecalciferol, vitamin E group such as α-tocopherol, β-tocopherol, γ-tocopherol, dl-α-tocopherol acetate, dl-α-tocopherol nicotinate, and dl-α-tocopherol succinate, nicotinic acids such as vitamin H, vitamin P, nicotinic acid, and benzyl nicotinate, phantothenic acids such as calcium pantothenate, D-pantothenyl alcohol, pantothenyl ethyl ether, and acetyl pantothenyl ethyl ether, and the like Examples of the amino acids may include glycine, valine, leucine, isoleucine, serine, threonine, phenylalanine, arginine, lysine, aspartic acid, glutamic acid, cystine, cysteine, methionine, tryptophan, and the like.

Examples of the nucleic acid may include deoxyribonucleic acid and the like.

Examples of the hormone may include estradiol, ethenyl estradiol and the like.

The natural plant extract component, the seaweed extract component, and the herbal medicine component are not particularly limited, but one or more of components having effects such as whitening action, anti-aging action, aging improving action, skin beautifying action, antibacterial action, antiseptic action and the like is preferably selected and blended.

Specific examples of the components may include Angelica extract, Avocado extract, hydrangea leaf extract, Althaea extract, Arnica extract, Aloe extract, Apricot extract, Apricot nuclear extract, Ginko bilobae extract, Fennel extract, turmeric extract, oolong tea extract, rose fruit extract, echinacea leaf extract, scutellaria root extract, cork tree bark extract, coptis extract, barley extract, hypericum erectum extract, lamium album extract, watercress extract, orange extract, seaweed dry matter, seaweed extract, hydrolyzed elastin, hydrolyzed wheat powder, hydrolyzed silk, chamomilla extract, carrot extract, artemisia capillaris flower extract, licorice extract, carcade extract, pyracantha fortuneana fruit extract, kiwi extract, kina extract, cucumber extract, guanosine, gardenia extract, sasa veitchii extract, sophora angustifolia root extract, walnut extract, grapefruit extract, clematis extract, chlorella extract, hoe extract, gentian extract, tea extract, yeast extract, burdock extract, rice bran fermentation extract, rice germ oil, comfrey extract, collagen, lingonberry extract, asiasarum extract, bupleurum falcatum extract, saitai extract, sage extract, soapwort extract, bamboo grass extract, Chinese Hawthorn extract, Japanese pepper extract, Shiitake extract, rehmannia root extract, Ilithospermum root extract, perilla extract, Tillia japonica extract, Filipendula multijuga extract, peony extract, sweet flag root extract, betula platyphylla extract, Horsetail extract, Hedra helix extract, Hawthorn extract, Bourtree extract, achillea millefolium extract, menthe piperita extract, Sage extract, mallow extract, cnidium officinale extract, Swertia japonica Makino extract, soybean extract, jujube extract, thyme extract, tea extract, clove extract, Chigaya extract, citrus unshiu peel extract, lacutilobum extract, *Calendula officinalis* extract, peach kernel extract, sour orange extract, houttuynia cordata extract, tomato extract, natto extract, carrot extract, garlic extract, bramble extract, hibiscus extract, ophiopogon tuber extract, lotus extract, parsley extract, honey, hamamelis extract, Parietaria extract, isodon japonicus extract, bisabolol, loquat extract, coltsfoot extract, butterbur sprout extract, poria sclerotium extract, butcher bloom extract, grape extract, propolis, sponge gourd extract, safflower extract, peppermint extract, lime tree extract, paeonia suffruticosa root extract, hop extract, pear extract, horse chestunut extract, skunk cabbage extract, Mukurossi peel extract, Melissa extract, peach extract, cornflower extract, Eucalyptus extract, strawberry geranium extract, citron extract, coix seed extract, mugwort extract, lavender extract, apple extract, lettuce extract, lemon extract, Chinese milk vetch extract, rose extract, rosemary extract, Roman chamomile extract, royal jelly extract, and the like.

These extracts may be water-soluble or oil-soluble.

The hair cosmetic product of the present invention may further include water.

Therefore, the hair cosmetic product of the present invention can take a form of emulsion such as an oil-in-water emulsion or a water-in-oil emulsion.

In this case, the hair cosmetic product of the present invention exhibits excellent emulsion stability and use feeling.

EXAMPLES

Hereinafter, the present invention will be described in detail by way of examples and comparative examples, but these examples do not limit the present invention described in the claims. In the examples, the viscosity is a measurement value at 25° C., the part representing the blending amount means parts by weight, and % representing the content means % by weight.

The average particle diameter of the emulsion particles was measured by a dynamic light scattering method at 25° C. using a submicron particle analyzer (COULTER MODEL N4 MD manufactured by Coulter Electronics Co., Ltd.) and calculated by a monodisperse mode analysis.

The content of octamethylcyclotetrasiloxane and decamethylcyclopentasiloxane in the prepared oil-in-water type silicone emulsion was measured using gas chromatography (manufactured by Shimadzu Corporation: GC-2010) by weighing 0.5 g of sample, adding 5 ml of methanol, 10 ml of hexane and 10 μl of n-dodecane and stirring them for several minutes, gently adding 10 ml of ultrapure water after standing overnight, and then sampling a hexane layer.

In addition, polydimethylsiloxane capped at both molecular chain terminals with a hydroxydimethylsiloxy group was prepared by appropriately mixing or not mixing polydimethylsiloxane which is capped at both molecular chain terminals with a linear hydroxydimethylsiloxy group and has a viscosity of 2,400 mPa·s with polydimethylsiloxane which is capped at both molecular terminals with a hydroxydimethylsiloxy group and has a viscosity of 80 mPa·s. The content of water in the nonionic surfactant used in the examples is 0%.

Example 1

An aqueous emulsifier solution obtained by mixing 9 parts of ethanol-containing product (stearyltrimethylammonium chloride/ethanol/water=70/24/6) of stearyltrimethylammonium chloride, 1.5 parts of polyoxyethylene (20 mol) sorbitan monooleate (HLB=14.9), 2 parts of phenoxyethanol, and 12 parts of water in advance was added to 100 parts of mixture of polydimethylsiloxane which is capped at both molecular chain terminals with hydroxydimethylsiloxy group and has a viscosity of 600 mPa·s and mixed. After emulsification is performed using a colloid mill, 75.5 parts of water was added and diluted to obtain an organopolysiloxane emulsion A (average polymerization number: 192).

Example 2

The emulsion was prepared by the same procedure as in Example 1, except that 1.5 parts of polyoxyethylene (20 mol) sorbitan monooleate of Example 1 was changed to 1.5 parts of polyglyceryl monolaurate (10 mol) (HLB=15.5).

Example 3

The emulsion was prepared by the same procedure as in Example 1, except that 100 parts by weight of a mixture of polydimethylsiloxane which is capped at both molecular chain terminals with a hydroxydimethylsiloxy group and has a viscosity of 600 mPa·s of Example 1 was changed to 100 parts by weight (average polymerization number: 328) of linear polydimethylsiloxane which is capped at both molecular terminals with hydroxydimethylsiloxy group and has a viscosity of 2,400 mPa·s.

Example 4

The aqueous emulsifier solution obtained by mixing 9 parts of ethanol-containing product (stearyltrimethylammonium chloride/ethanol/water=70/24/6) of stearyltrimethylammonium chloride, 2.5 parts of polyoxyethylene (20 mol) sorbitan monooleate (HLB=14.9), and 12 parts of water in advance was added to a mixture (average polymerization number: 237) of linear polydimethylsiloxane which is capped at both molecular chain terminals with hydroxydimethylsiloxy group and has a viscosity of 1,000 mPa·s and mixed. After emulsification is performed using a colloid mill, 76.5 parts of water was added and diluted to obtain an emulsion.

Example 5

The emulsion was prepared by the same procedure as in Example 4, except that 2.5 parts of polyoxyethylene (20 mol) sorbitan monooleate (HLB=14.9) of Example 4 was changed to 2.5 parts of polyoxyethylene-polyoxypropylene block copolymer (HLB=16.0).

Example 6

The emulsion was prepared by the same procedure as in Example 4, except that 2.5 parts of polyoxyethylene (20 mol) sorbitan monooleate (HLB=14.9) of Example 4 was changed to 2.5 parts of polyglyceryl monolaurate (10 mol) (HLB=15.5).

Example 7

The emulsion was prepared by the same procedure as in Example 4, except that 100 parts by weight of a mixture of polydimethylsiloxane which is capped at both molecular chain terminals with a hydroxydimethylsiloxy group and has a viscosity of 1,000 mPa·s of Example 4 was changed to 100 parts by weight (average polymerization number: 328) of linear polydimethylsiloxane which is capped at both molecular terminals with hydroxydimethylsiloxy group and has a viscosity of 2,400 mPa·s.

Example 8

The emulsion was prepared by the same procedure as in Example 7, except that 2.5 parts of polyoxyethylene (20 mol) sorbitan monooleate (HLB=14.9) of Example 7 was changed to 2.5 parts of polyoxyethylene-polyoxypropylene block copolymer (HLB=16.0).

Example 9

The aqueous emulsifier solution obtained by mixing 8.9 parts of ethanol-containing product (stearyltrimethylammonium chloride/ethanol/water=70/24/6) of stearyltrimethylammonium chloride which had been previously prepared, 2.5 parts of polyoxyethylene (20 mol) sorbitan monooleate (HLB=14.9), and 10 parts of water was added to 100 parts of weight (average polymerization number: 212) of polydimethylsiloxane which is capped at both molecular terminals with trimethylsilyl group and has a viscosity of 1,000 mPa·s and mixed. After phase inversion emulsification is performed using a colloid mill, 128.6 parts of water was added and diluted to obtain an emulsion.

Example 10

The emulsion was prepared by the same procedure as in Example 9, except that 2.5 parts of polyoxyethylene (20 mol) sorbitan monooleate (HLB=14.9) of Example 9 was changed to 1.25 parts of polyoxyethylene-polyoxypropylene block copolymer (HLB=16.0) and 128.6 parts of water used for dilution was changed to 129.87 parts.

Example 11

The emulsion was prepared by the same procedure as Example 10, except that 1.25 parts of polyoxyethylene-polyoxypropylene block copolymer (HLB=16.0) of Example 10 was changed to 2.5 parts, 10 parts of water used for the aqueous emulsifier solution was changed to 15 parts and 129.87 parts of water used for dilution was changed to 123.58 parts.

Example 12

The emulsion was prepared by the same procedure as in Example 9, except that 8.9 parts of ethanol-containing product (stearyl trimethyl ammonium chloride/ethanol/water=70/24/6) of the stearyl trimethyl ammonium chloride of Example 9 was changed to 10.7 parts, 2.5 parts of polyoxyethylene (20 mol) sorbitan monooleate (HLB=14.9) was changed to 2.5 parts of polyoxyethylene (50 mol) oleyl ether (HLB=18.0), 10 parts of water used for the aqueous emulsifier solution was added to 12.5 parts, and 128.58 parts of water used for dilution was changed to 124.29 parts.

Example 13

The emulsion was prepared by the same procedure as in Example 12, except that 2.5 parts of polyoxyethylene (50 mol) oleyl ether (HLB=18.0) of Example 12 was changed to 2.5 parts of polyoxyethylene (55 mol) stearate (HLB=18.0).

Example 14

The aqueous emulsion solution obtained by mixing 25.2 parts of water-containing product (stearyltrimethylammonium chloride/water=25/75) of stearyltrimethylammonium chloride which had been previously prepared, 2 parts of polyoxyethylene-polyoxypropylene block copolymer (HLB=16.0), and 2 parts of phenoxyethanol was added to 100 parts of weight (average polymerization number: 212)

of polydimethylsiloxane which is capped at both molecular terminals with trimethylsilyl group and has a viscosity of 1,000 mPa·s and mixed. After the phase inversion emulsification is performed using the colloid mill, 71.8 parts of water was added and diluted.

Example 15

The aqueous emulsifier solution obtained by mixing 7.8 parts of ethanol-containing product (stearyltrimethylammonium chloride/isopropanol/water=80/18/2) of stearyltrimethylammonium chloride, 1.5 parts of polyoxyethylene (20 mol) sorbitan monooleate (HLB=14.9), 2 parts of phenoxyethanol, and 12 parts of water in advance was added to polydimethylsiloxane (average polymerization number: 192) which is capped at both molecular chain terminals with hydroxydimethylsiloxy group and has a viscosity of 600 mPa·s and mixed. After the phase inversion emulsification is performed using the colloid mill, 76.7 parts of water was added and diluted.

Comparative Example 1

The aqueous emulsion solution obtained by mixing 10 parts of ethanol-containing product (stearyltrimethylammonium chloride/ethanol/water=75/24/6) of stearyltrimethylammonium chloride and 11 parts of water was added to 100 parts by weight (average polymerization number: 328) of polydimethylsiloxane which is capped at both molecular chain terminals with hydroxydimethylsiloxy group and has a viscosity of 2,400 mPa·s. Although phase inversion emulsification is performed using a colloid mill, the emulsification could not be performed.

Comparative Example 2

The aqueous emulsifier solution obtained by mixing 9 parts of ethanol-containing product (stearyltrimethylammonium chloride/ethanol/water=70/24/6) of stearyltrimethylammonium chloride, 1.5 parts of polyoxyethylene (20 mol) sorbitan monooleate (HLB=14.9), 2 parts of phenoxyethanol, and 12 parts of water in advance was added to 100 parts of weight (average polymerization number: 1,294) of polydimethylsiloxane which is capped at both molecular terminals with trimethylsilyl group and has a viscosity of 1,000,000 mPa·s and mixed. After the phase inversion emulsification is performed using the colloid mill, 75.5 parts of water was added and diluted to obtain the emulsion.

In the prescription examples, the numerical values after each component name represent parts by weight.

In addition, the balance represents the remaining parts by weight when the whole is taken as 100 parts by weight.

Prescription Example 1

(Transparent Type Shampoo 1)
(Component)
1. Purified water balance
2. Polyquaternium-10 (3% aqueous solution) 10.0
3. Citric acid 0.06
4. EDTA-2Na 0.1
5. Glycerin 1.5
6. Cocamide MEA 1.0
7. Sodium laureth sulfate (27% aqueous solution) 30.0
8. Laureth-6 carboxylic acid Na (24% aqueous solution) 10.0
9. Cocamidopropyl betaine, NaCl (30% aqueous solution) 10.0
10. Polyquaternium-7 (9% aqueous solution) 3.0
11. Proper amount of antiseptic
12. Cocamide MEA 1.0
13. Organopolysiloxane emulsion A (prepared in Example 1) 6.0
14. Proper amount of citric acid (10% aqueous solution)
(Preparation Procedure)
Step 1 Heat, mix and dissolve components 1 to 6.
Step 2 Add components 7 to 9 to the composition obtained in Step 1 and heat and mix it.
Step 3 Cool the composition obtained in Step 2 and add components 10 to 13. Add component 14 and adjust the pH, if necessary.

Prescription Example 2

1. Purified water balance
2. Polyquaternium-10 (3% aqueous solution) 15.0
3. EDTA-2Na 0.1
4. Sodium Benzoate 0.3
5. Glycerin 2.0
6. Cocamide MEA 2.0
7. Sodium cocoyl methyl taurate (30% aqueous solution) 16.0
8. Sodium laureth sulfate (25% aqueous solution) 30.0
9. Cocamidopropyl betaine, NaCl (30% aqueous solution) 10.0
10. Cocamide MEA 1.0

TABLE 1

| | Example 1 | Example 2 | Example 3 | Example 4 | Example 5 | Example 6 | Example 7 | Example 8 |
|---|---|---|---|---|---|---|---|---|
| Average particle diameter (nm) | 288 | 310 | 422 | 310 | 397 | 388 | 412 | 396 |
| pH | 6.6 | 6.1 | 6.7 | 6.6 | — | — | — | — |
| Stability at 25° C. | Stable for 2 months or more | Stable for 2 months or more | Stable for 2 months or more | Stable for 2 months or more | Stable for 2 months or more | Stable for 2 months or more | Stable for 2 months or more | Stable for 2 months or more |
| Stability at 50° C. | Stable for 2 months or more | Stable for 2 months or more | Stable for 2 months or more | Stable for 2 months or more | Stable for 2 months or more | Stable for 2 months or more | Stable for 2 months or more | Stable for 2 months or more |
| D4 (%) after storage at 50° C./1 month | 0.01 | 0.01 | 0.01 | 0.01 | 0.01 | 0.01 | 0.01 | 0.01 |
| D5 (%) after storage at 50° C./1 month | 0.01 | 0.01 | 0.01 | 0.01 | 0.01 | 0.01 | 0.01 | 0.01 |

11. Cyclohexane-1,4-dicarboxylic acid bisethoxydiglycol 2.0
12. Purified water 4.0
13. Polyquaternium-7 (9% aqueous solution) 1.0
14. Phenoxyethanol 0.5
15. Organopolysiloxane emulsion A (prepared in Example 1) 6.0
16. Proper amount of citric acid (10% aqueous solution)
(Transparent Shampoo 2)
(Component)
(Preparation Procedure)
Step 1 Heat, mix and dissolve components 1 to 8.
Step 2 Add components 9 to 11 to the composition obtained in Step 1 and heat and mix it.
Step 3 Cool the composition obtained in Step 2 and add a mixture of components 12 and 13, and a mixture of components 14 and 15. Add component 16 and adjust the pH, if necessary.

Prescription Example 3

(Pearl Type Shampoo 1)
(Component)
1. Purified water balance
2. Polyquaternium-10 (3% aqueous solution) 10
3. Citric acid 0.06
4. EDTA-2Na 0.1
5. Glycerin 1.5
6. Cocamide MEA 2.0
7. Distearic acid glycol 2.0
8. Sodium laureth sulfate (27% aqueous solution) 30.0
9. Laureth-6 carboxylic acid Na (24% aqueous solution) 10.0
10. Cocamidopropyl betaine, NaCl (30% aqueous solution) 10.0
11. Polyquaternium-7 (9% aqueous solution) 3.0
12. Proper amount of antiseptic
13. Cocamide MEA 1.0
14. Organopolysiloxane emulsion A (prepared in Example 1) 6.0
15. Proper amount of citric acid (10% aqueous solution)
(Preparation Procedure)
Step 1 Heat, mix and dissolve components 1 to 7.
Step 2 Add components 8 to 10 to the composition obtained in Step 1 and heat and mix it.
Step 3 Cool the composition obtained in Step 2 and add components 11 to 14. Add component 14 and adjust the pH, if necessary.

Prescription Example 4

(Conditioner)
(Component)
1. Stearyl trimethyl ammonium chloride (63% aqueous solution) 1.8
2. Cetyl alcohol 2.4
3. Octyldodecanol 0.5
4. Cetyl ethylhexanoate 0.6
5. Squalane 0.2
6. Purified water 77.4
7. Glycerin 2.0
8. Proper amount of antiseptic
9. Organopolysiloxane emulsion A (prepared in Example 1) 6.0
10. Proper amount of citric acid (10% aqueous solution)
11. Purified water balance (Preparation Procedure)
Step 1 Heat, mix and dissolve components 1 to 5.
Step 2 Heat and dissolve components 6 and 7.
Step 3 Add the composition obtained in Step 2 to the composition obtained in Step 1 and emulsify it.
Step 4 Cool the composition obtained in Step 3 and add components 8 and 9. Add component 10 and adjust the pH, if necessary.
Step 5 Add component 11.

Prescription Example 5

(Hair Treatment Leave-on Type)
(Component)
1. Cetyl alcohol 4.0
2. Mineral oil 1.0
3. Steartrimonium chloride 1.0
4. Behentrimonium Chloride 0.2
5. Glycerin 2.0
6. EDTA-2Na 0.1
7. Purified water balance
8. Panthenol 0.1
9. Tocopherol 0.04
10. Lysine HCl 0.02
11. Glycine 0.02
12. Histidine 0.02
13. Organopolysiloxane emulsion A (prepared in Example 1) 6.0
14. Proper amount of antiseptic
15. Proper amount of perfume
(Preparation Procedure)
Step 1 Heat, mix and dissolve components 1 to 4.
Step 2 Heat, mix and dissolve components 5 to 7.
Step 3 Add the composition obtained in Step 2 to the composition obtained in Step 1 and emulsify it.
Step 4 Cool the composition obtained in Step 3 and add components 8 to 15. [Prescription Example 6]
(Hair Color Oxidation Type)
First Agent
(Component)
1. Steareth-2 3.0
2. Steareth-21 2.0
3. PPG-15 stearyl 5.0
4. Cetostearyl alcohol 4.0
5. Behenyl alcohol 2.0
6. Behenyl trimethyl ammonium chloride 0.8
7. Purified water balance
8. EDTA-2Na 0.5
9. Anhydrous sodium sulfite 0.5
10. Sodium ascorbate 0.1
11. 1,3-butylene glycol 3.0
12. Paraphenylene diamine 0.25
13. Paraaminophenol 0.1
14. Metaaminophenol 0.05
15. Organopolysiloxane emulsion A (prepared in Example 1) 6.0
16. Polyquaternium-39 0.3
17. Ammonium bicarbonate 2.0
18. Strong ammonia water 5.0
(Preparation Procedure)
Step 1: Heat, mix and dissolve components 1 to 6.
Step 2: Heat, mix and dissolve components 7 to 14.
Step 3: Add the composition obtained in Step 1 to the composition obtained in Step 2 and emulsify it.
Step 4: Sequentially add components 15 to 18 to the composition obtained in Step 3.

Second Agent
(Component)
1. Cetostearyl alcohol 4.5
2. Sodium lauryl sulfate 0.5
3. Proper amount of antiseptic
4. Etidronic acid 0.1
5. Disodium hydrogen phosphate 0.3
6. Purified water balance
7. Hydrogen peroxide solution (35% aqueous solution) 17.14
8. Proper amount of phosphoric acid
(Preparation Procedure)
Step 1: Heat and dissolve component 1.
Step 2: Heat, mix and dissolve components 2 to 6.
Step 3: Add the composition obtained in Step 1 to the composition obtained in Step 2 and emulsify it.
Step 4: Cool the composition obtained in Step 3, add component 7 and, if necessary, component 8.

INDUSTRIAL APPLICABILITY

The oil-in-water type organopolysiloxane emulsion of the present invention can be used for hair cosmetics such as rinse, a conditioner, and a treatment agent due to high stability of emulsion and adsorption of particles to hair.

The invention claimed is:

1. An oil-in-water type organopolysiloxane emulsion, comprising:
(A) 100 parts by weight of a dimethylpolysiloxane having a viscosity of 2 to 50,000 mPa·s at 25° C.;
(B) 0.5 to 30 parts by weight of a cationic surfactant;
(C) 0.1 to 10 parts by weight of a nonionic surfactant;
(D) 11 to 550 parts by weight of water; and
(E) 0.1 to 20 parts by weight of ethanol;
wherein a content of component (C) is equal to or less than a content of component (B);
wherein an average particle diameter of component (A) in the emulsion is 600 nm or less; and
wherein octamethylcyclotetrasiloxane and decamethylcyclopentasiloxane are present and respective contents of the octamethylcyclotetrasiloxane and the decamethylcyclopentasiloxane are 0.5% or less by weight in the emulsion.

2. The oil-in-water type organopolysiloxane emulsion according to claim 1, wherein component (B) is at least one quaternary ammonium salt selected from the group consisting of stearyltrimethylammonium chloride, distearyldimethylammonium chloride, stearyldimethylbenzylammonium chloride, dioleyldimethylammonium chloride, behenyltrimethylammonium chloride, dibehenyldimethylammonium chloride, and behenyldimethylbenzylammonium chloride.

3. The oil-in-water type organopolysiloxane emulsion according to claim 1, wherein component (C) is at least one nonionic surfactant selected from the group consisting of a sorbitan fatty acid ester, a polyoxyethylene sorbitan fatty acid ester, a polyoxyethylene sorbitol fatty acid ester, a glycerin fatty acid ester, a polyoxyethylene hydrogenated castor oil, a polyglycerin fatty acid ester, and a polyoxyethylene-polyoxypropylene block copolymer.

4. The oil-in-water type organopolysiloxane emulsion according to claim 1, wherein respective contents of the octamethylcyclotetrasiloxane and the decamethylcyclopentasiloxane are 0.25% or less by weight in the emulsion.

5. A method for producing an oil-in-water type organopolysiloxane emulsion, said method comprising:
emulsifying under shear force the following components;
(A) 100 parts by weight of a dimethylpolysiloxane having a viscosity of 2 to 50,000 mPa·s at 25° C.,
(B) 0.5 to 30 parts by weight of a cationic surfactant,
(C) 0.1 to 10 parts by weight of a nonionic surfactant,
(D) 1 to 50 parts by weight of water, and
(E) 0.1 to 20 parts by weight of ethanol;
wherein an amount of component (C) is equal to or less than an amount of component (B) utilized in the method, and an amount of component (D) is 3 times or less than a combined amount of components (B) and (C) utilized in the method;
adding 10 to 500 parts by weight of water to give a mixture; and
subjecting the mixture to phase inversion emulsification to produce the oil-in-water type organopolysiloxane emulsion;
wherein octamethylcyclotetrasiloxane and decamethylcyclopentasiloxane are present and respective contents of the octamethylcyclotetrasiloxane and the decamethylcyclopentasiloxane are 0.5% or less by weight in the emulsion.

6. A cosmetic raw material comprising the oil-in-water type organopolysiloxane emulsion according to claim 1.

7. The cosmetic raw material according to claim 6, wherein the raw material is further defined as a raw material for a hair cosmetic product.

8. A cosmetic product comprising the cosmetic raw material according to claim 6.

9. The method according to claim 5, wherein component (B) is at least one quaternary ammonium salt selected from the group consisting of stearyltrimethylammonium chloride, distearyldimethylammonium chloride, stearyldimethylbenzylammonium chloride, dioleyldimethylammonium chloride, behenyltrimethylammonium chloride, dibehenyldimethylammonium chloride, and behenyldimethylbenzylammonium chloride.

10. The method according to claim 5, wherein component (C) is at least one nonionic surfactant selected from the group consisting of a sorbitan fatty acid ester, a polyoxyethylene sorbitan fatty acid ester, a polyoxyethylene sorbitol fatty acid ester, a glycerin fatty acid ester, a polyoxyethylene hydrogenated castor oil, a polyglycerin fatty acid ester, and a polyoxyethylene-polyoxypropylene block copolymer.

11. The method according to claim 5, wherein respective contents of the octamethylcyclotetrasiloxane and the decamethylcyclopentasiloxane are 0.25% or less by weight in the emulsion.

12. The method accordingly to claim 5, wherein an average particle diameter of component (A) in the emulsion is 600 nm or less.

13. The oil-in-water type organopolysiloxane emulsion according to claim 1, wherein component (A) has a viscosity of 10 to 50,000 mPa·s at 25° C.

14. The method accordingly to claim 5, wherein component (A) has a viscosity of 10 to 50,000 mPa·s at 25° C.

15. The oil-in-water type organopolysiloxane emulsion according to claim 4, wherein respective contents of the octamethylcyclotetrasiloxane and the decamethylcyclopentasiloxane are 0.1% or less by weight in the emulsion.

16. The method according to claim 11, wherein respective contents of the octamethylcyclotetrasiloxane and the decamethylcyclopentasiloxane are 0.1% or less by weight in the emulsion.

* * * * *